(12) United States Patent
Saiki et al.

(10) Patent No.: US 8,709,346 B2
(45) Date of Patent: Apr. 29, 2014

(54) ANALYSIS DEVICE AND AN ANALYSIS APPARATUS USING THE ANALYSIS DEVICE

(75) Inventors: Hiroshi Saiki, Ehime (JP); Masanori Tanaka, Ehime (JP)

(73) Assignee: Panasonic Corporation, Osaka (JP)

( * ) Notice: Subject to any disclaimer, the term of this patent is extended or adjusted under 35 U.S.C. 154(b) by 357 days.

(21) Appl. No.: 12/945,215

(22) Filed: Nov. 12, 2010

(65) Prior Publication Data
US 2011/0058985 A1 Mar. 10, 2011

Related U.S. Application Data

(62) Division of application No. 12/058,226, filed on Mar. 28, 2008, now Pat. No. 7,854,893.

(51) Int. Cl.
*G01N 33/00* (2006.01)

(52) U.S. Cl.
USPC ............. 422/72; 422/405; 422/68.1; 422/506

(58) Field of Classification Search
USPC ........................... 422/50, 405, 68.1, 501, 506
See application file for complete search history.

(56) References Cited

U.S. PATENT DOCUMENTS

| | | | |
|---|---|---|---|
| 5,160,702 A | 11/1992 | Kopf-Sill et al. | |
| 6,033,914 A | 3/2000 | Boyd et al. | |
| 6,063,589 A | 5/2000 | Kellogg et al. | |
| 6,632,399 B1 | 10/2003 | Kellogg et al. | |
| 6,656,430 B2 | 12/2003 | Sheppard et al. | |
| 6,752,961 B2 | 6/2004 | Kopf-Sill et al. | |
| 7,390,464 B2 | 6/2008 | Kido et al. | |
| 7,857,141 B2 * | 12/2010 | Park et al. | 209/199 |
| 2004/0191125 A1 | 9/2004 | Kellogg et al. | |
| 2009/0169430 A1 * | 7/2009 | Yamamoto et al. | 422/72 |
| 2009/0238724 A1 * | 9/2009 | Yamamoto et al. | 422/68.1 |

FOREIGN PATENT DOCUMENTS

| | | |
|---|---|---|
| JP | 5-508709 | 12/1993 |
| WO | 91/18656 | 12/1991 |
| WO | WO 2007052648 A1 * | 5/2007 |
| WO | WO 2007116909 A1 * | 10/2007 |

* cited by examiner

*Primary Examiner* — Sam P Siefke
(74) *Attorney, Agent, or Firm* — Wenderoth, Lind & Ponack, L.L.P.

(57) ABSTRACT

An analysis device includes a separation chamber, a holding channel, a mixing chamber connected to the holding channel, an overflow channel connected between the holding channel and the separation chamber, a sample overflow chamber into which a sample solution remaining in the separation chamber is discharged, and a joint channel connecting the separation chamber and the sample overflow chamber. After the separated solution component fills the overflow channel with priority, a separated solid component is transferred to the holding channel via the overflow channel, and a predetermined amount of the solid component is measured. The solid component in the holding channel is transferred to the mixing chamber by a centrifugal force, and simultaneously, the sample solution remaining in the separation chamber is discharged to the sample overflow chamber by the siphon effect of the joint channel.

12 Claims, 23 Drawing Sheets

//ANALYSIS DEVICE AND AN ANALYSIS APPARATUS USING THE ANALYSIS DEVICE

CROSS-REFERENCE TO RELATED APPLICATION

This application is a divisional of U.S. application Ser. No. 12/058,226, filed Mar. 28, 2008 now U.S. Pat. No. 7,854,893, the entirety of which is incorporated herein by reference.

FIELD OF THE INVENTION

The present invention relates to an analysis device for optically analyzing a biological fluid, and an analysis apparatus using the analysis device. To be specific, the invention relates to a method of collecting a solution component or a solid component in an analysis device which is used for component measurement for a biological fluid in an optical analysis apparatus, and more specifically, to a method of collecting a plasma component or a blood cell component in blood.

BACKGROUND OF THE INVENTION

Conventionally, as a method for optically analyzing a biological fluid, an analysis method using a microdevice having fluid channels has been known. A microdevice can control a fluid by using a rotation device, and it can perform measurement of a sample solution, separation of a solid component, and transfer/distribution of a separated fluid by utilizing a centrifugal force, and therefore, it can perform various kinds of biochemical analysis.

As a device for transferring a sample solution utilizing a centrifugal force, there is a rotation analysis device shown in FIG. 23 which comprises a large-sized fluid chamber 81, a measurement chamber 82 which is connected to the large-sized fluid chamber 81 and is disposed radially outer than the fluid chamber 81, an overflow chamber 83 connected to the measurement chamber 82, a reception chamber 84 disposed radially outer than the measurement chamber 82, and a capillary tube joint means 85 for supplying a fluid from the measurement chamber 82 to the reception chamber 84.

The capillary tube joint means 85 includes a siphon 86 having a capillary tube structure, and it is positioned such that the distance from the center of the rotation analysis device to an elbow-shaped bend portion of the siphon 86 is substantially equal to the distance from the center of the rotation analysis device to a radially innermost point of the measurement chamber 82. Since the capillary tube force is smaller than the centrifugal force during rotation of the rotation analysis device, the fluid/air interface matches the shape of a rotation cylindrical body which has the same axis line as that of the rotation analysis device and has a radius as long as the distance from the center of the rotation analysis device to the radially innermost point of the measurement chamber 82, and the measurement chamber 82 is filled with the sample solution and the excessive sample solution flows into the overflow chamber 83.

When the rotation analysis device is stopped, the sample solution filled in the measurement chamber 82 flows into the capillary tube joint means 85 due to a capillary force, and the siphon starts to operate by rotating the analysis device again, and thereby the solution existing in the measurement chamber 82 is discharged to the reception chamber 84 (refer to Japanese Published Patent Application No. Hei.5-508709).

At this time, if the sample solution contains a solid component, the solid component is precipitated by performing centrifugal separation in the measurement chamber 82 or the reception chamber 84, and thereafter, the capillary tube having the siphon structure is connected to a radially inner part of the chamber, whereby only the solution component in the sample solution can be transferred to the next process.

In the above-described conventional construction, although only the solution component in the sample solution can be transferred by only adjusting the position to which the capillary tube is connected after performing the centrifugal separation, since the solid component is precipitated in the outer circumference direction, the solid component or the high-concentration solid component solution cannot be transferred by the transfer using the siphon.

Further, when only the solution component is transferred by the capillary tube having the siphon structure, the remaining solution again flows into the capillary tube with stopping of the rotation, and the solution in the capillary tube is again transferred by the next rotation, thereby adversely affecting the measurement precision due to variation in the solution amount or flow-in of the solid component into the capillary tube.

SUMMARY OF THE INVENTION

The present invention is made to solve the above-described problems and has for its object to provide an analysis device which can perform transfer of a solid component or a high-concentration solid component solution, and can prevent a sample solution which remains when a part of the sample solution has been transferred from flowing in afterward, and an analysis apparatus using the analysis device.

Other objects and advantages of the invention will become apparent from the detailed description that follows. The detailed description and specific embodiments described are provided only for illustration since various additions and modifications within the scope of the invention will be apparent to those of skill in the art from the detailed description.

In order to solve the above-described problems, according to a first aspect of the present invention, there is provided an analysis device in which a sample solution to be analyzed is stored and the sample solution can be transferred, comprising a separation chamber for separating the sample solution into a solution component and a solid component by using a centrifugal force that is generated by rotation of the analysis device, a holding channel to which a part of the solid component separated in the separation chamber is transferred and stored, and an overflow channel which is disposed between the holding channel and the separation chamber, and connected to a joint channel for transferring the sample solution stored in the separation chamber, wherein, after the solution component that is separated in the separation chamber and exists in the joint channel flows into the overflow channel with priority, the solid component separated in the separation chamber is filled in the overflow channel via the joint channel, and thereafter, the solid component in the separation chamber flows into the holding channel from the joint channel via the overflow channel, whereby a part of the solid component is held in the holding channel.

According to a second aspect of the present invention, the analysis device according to the first aspect further includes an overflow chamber to which the sample solution filled in the overflow channel is discharged, and the overflow chamber is connected to the overflow channel via a junction part, transfer of the sample solution from the joint channel to the overflow channel is performed by a capillary force, and an opening area of the overflow channel at the junction part between the overflow channel and the overflow chamber is larger than that of the holding channel.

According to a third aspect of the present invention, the analysis device according to the first aspect further includes an overflow chamber to which the sample solution filled in the overflow channel is discharged, and the overflow chamber is connected to the overflow channel via a junction part, transfer of the sample solution from the joint channel to the overflow channel is performed by pumping, air in the overflow channel and the joint channel is sucked from an air hole provided on the overflow chamber by a suction pump, and the solution component existing in the joint channel is transferred with priority to the junction part between the overflow channel and the overflow chamber due to a pressure difference caused by the suction.

According to a fourth aspect of the present invention, the analysis device according to the first aspect further includes a mixing chamber connected to the holding channel, for mixing the solid component with a dilute solution or a reagent solution, and a dilute solution storage chamber connected to the mixing chamber, in which the dilute solution or the reagent solution is stored.

According to a fifth aspect of the present invention, in the analysis device according to the first aspect, the holding channel measures the solid component by its volume.

According to a sixth aspect of the present invention, there is provided an analysis device in which a sample solution to be analyzed is stored and the sample solution can be transferred, comprising a fluid storage chamber in which the sample solution is stored, a holding channel connected to the fluid storage chamber, for transferring the sample solution from the fluid storage chamber by a capillary force, and holding a part of the sample solution, a fluid holding chamber for holding the sample solution in the holding channel which has been transferred by an external force, and a sample overflow chamber which is positioned outer than the fluid storage chamber with respect to an axial center of the analysis device when the analysis device is rotated around the axial center, and is connected to the fluid storage chamber via a capillary channel having a siphon structure.

According to a seventh aspect of the present invention, in the analysis device according to the sixth aspect, the external force is a centrifugal force that is generated by rotation of the analysis device.

According to an eighth aspect of the present invention, in the analysis device according to the sixth aspect, the external force is a pressure that is generated by introduction of a gas from an air hole provided at a fluid separation position of the holding channel.

According to a ninth aspect of the present invention, in the analysis device according to the sixth aspect, the fluid storage chamber includes a separation chamber for separating the sample solution into a solution component and a solid component by using a centrifugal force that is generated by rotation of the analysis device, and the holding channel transfers only the solution component that is separated from the sample solution, from the separation chamber via the joint channel.

According to a tenth aspect of the present invention, in the analysis device according to the sixth aspect, the holding channel measures the solution to be held by its volume.

According to an eleventh aspect of the present invention, in the analysis device according to the sixth aspect, the fluid storage chamber includes a separation chamber for separating the sample solution into a solution component and a solid component by using a centrifugal force that is generated by rotation of the analysis device, and the analysis device further includes a holding channel for holding a part of the solid component separated in the separation chamber, an overflow channel which is disposed between the holding channel and the separation chamber and is connected to the separation chamber by a junction channel, and an overflow chamber connected to the overflow channel.

According to a twelfth aspect of the present invention, in the analysis device according to the eleventh aspect, the overflow chamber is connected to the overflow channel via a junction part, the holding channel and said overflow channel have a capillary tube size which generates a capillary flow of fluid, and an opening area of the overflow channel at the junction part between the overflow channel and the overflow chamber is larger than that of the holding channel.

According to a thirteenth aspect of the present invention, the analysis device according to the eleventh aspect further includes a solution component holding channel connected to the separation chamber, for holding a part of the solution component separated from the sample solution in the separation chamber, and a measurement cell for holding the solution component filled in the solution component holding channel, mixing/reacting the solution component with a reagent, and measuring an absorbance or a turbidity of the mixed solution.

According to a fourteenth aspect of the present invention, there is provided an analysis apparatus on which the analysis device according to the second aspect is mounted, including a rotation drive means for rotating the analysis device around its axial center, which apparatus comprises: separating a sample solution into a solution component and a solid component by rotating the analysis device in the state where the sample solution is stored in the separation chamber, transferring the solution component that has flowed into the joint channel from the separation chamber with priority to the junction part between the overflow channel and the overflow chamber by a capillary force by stopping the rotation of the analysis device, transferring the solid component stored in the separation chamber to the holding channel by a capillary force, and discharging the solution component and the solid component filled in the overflow channel and the junction part into the overflow chamber by rotating the analysis device.

According to a fifteenth aspect of the present invention, there is provided an analysis apparatus on which the analysis device according to the third aspect is mounted, including a rotation drive means for rotating the analysis device around its axial center, a pump for sucking the solution stored in the analysis device, and a junction mechanism for connecting the pump and the air hole of the analysis device, which apparatus comprises: separating a sample solution into a solution component and a solid component by rotating the analysis device in the state where the sample solution is stored in the separation chamber, after the rotation of the analysis device is stopped, connecting the junction mechanism to the air hole of the overflow chamber and sucking air with the pump, thereby to transfer the solution component that has flowed into the joint channel with priority to the junction part between the overflow channel and the overflow chamber, after the junction part is filled up, connecting the junction mechanism to the air hole of the holding chamber connected to the holding channel and sucking air with the pump, thereby to transfer the solid component in the separation chamber to the holding channel, and after the holding channel is introduced into the solid component, detaching the junction mechanism and rotating the analysis device again, thereby to discharge the solution component and the solid component filled in the overflow channel and the junction part into the overflow chamber.

According to a sixteenth aspect of the present invention, there is provided an analysis apparatus on which the analysis device according to the seventh aspect is mounted, including a rotation drive means for rotating the analysis device around its axial center, which apparatus comprises: transferring a sample solution to an outer circumference part of the fluid storage chamber by rotating the analysis device in which the sample solution is stored in the fluid storage chamber, sucking the sample solution out of the fluid storage chamber by a capillary force and storing it in the holding channel by stopping the rotation of the analysis device, sucking the sample solution out of the fluid storage chamber by a capillary force and storing it in the capillary channel having the siphon structure connected to the sample overflow chamber, and transferring the sample solution filled in the holding channel to the fluid holding chamber by rotating the analysis device, and discharging the sample solution in the fluid storage chamber into the sample overflow chamber by the siphon structure of the capillary channel.

According to a seventeenth aspect of the present invention, there is provided an analysis apparatus on which the analysis device according to the eighth aspect is mounted, including a rotation drive means for rotating the analysis device around its axial center, and a gas introduction mechanism for transferring the solution in the analysis device, which apparatus comprises: transferring a sample solution to an outer circumference part of the fluid storage chamber by rotating the analysis device in which the sample solution is stored in the fluid storage chamber, sucking the sample solution out of the fluid storage chamber by a capillary force and storing it in the holding channel by stopping the rotation of the analysis device, sucking the sample solution out of the fluid storage chamber by a capillary force and storing it in the capillary channel having the siphon structure connected to the sample overflow chamber, connecting the gas introduction mechanism to the air hole provided at the fluid separation position of the holding channel, and to the air hole provided at the inner circumference part of the fluid storage chamber, and supplying a gas from the gas introduction mechanism via the air hole so that the sample solution filled in the holding channel is separated at the fluid separation position and transferred to the fluid holding chamber, and discharging the sample solution in the fluid storage chamber into the sample overflow chamber by the siphon structure of the capillary channel.

According to the analysis device and the analysis apparatus of the present invention, the solid component or the high-concentration solid component solution which is obtained by performing the centrifugal separation can be transferred by a required amount. Further, the sample solution which remains when a part of the sample solution has been transferred can be prevented from flowing in afterward, thereby enhancing the measurement precision of the analysis device.

DETAILED DESCRIPTION OF THE INVENTION

Hereinafter, embodiments of analysis devices according to the present invention will be described in detail with reference to the drawings.

[Embodiment 1]

Hereinafter, an analysis device 101 according to a first embodiment and an analysis apparatus 1000 using the analysis device 101 will be described with reference to FIGS. 1 to 5.

Figure 1:
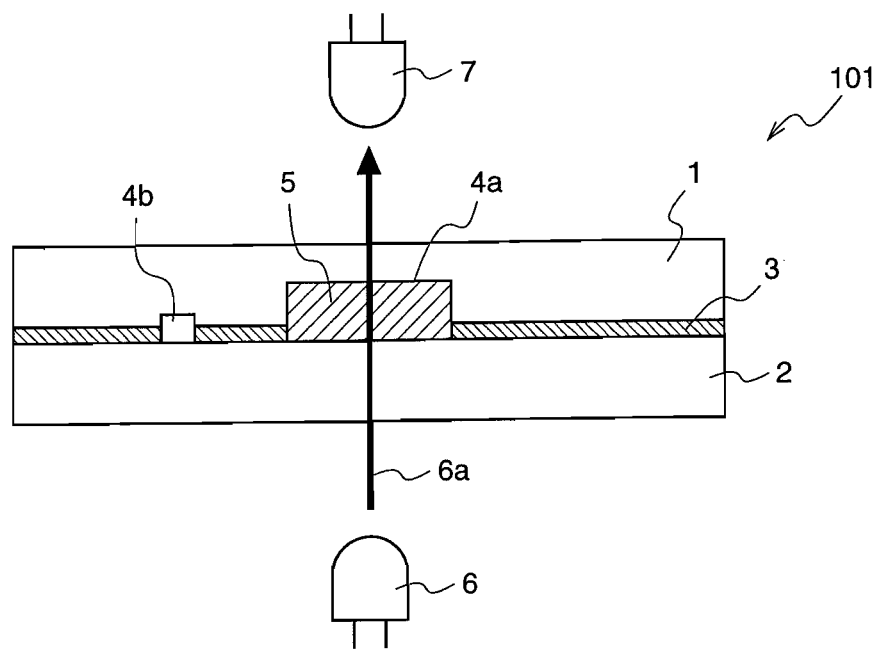
FIG. 1 is a schematic diagram illustrating the construction of an analysis device 101 according to a first embodiment of the present invention.

FIG. 1 is a schematic diagram illustrating the construction of the analysis device 101 according to the first embodiment of the present invention.

With reference to FIG. 1, the analysis device 101 comprises a substrate 1 having microchannels 4a and 4b, a flat substrate 2, and an adhesive layer 3 by which the both substrates are bonded together. Further, a reaction solution 5 is filled in the microchannel 4a among the microchannels which are formed by bonding the substrates 1 and 2 together.

The microchannels 4a and 4b on the substrate 1 are obtained by fabricating a concavo-convex microchannel pattern by injection molding. A sample solution to be analyzed is injected into the analysis device 101, and the sample solution can be transferred in the device 101 through the microchannels 4a and 4b.

In this first embodiment, the microchannel 4a is irradiated with a transmitted light 6a to optically analyze a reaction between the sample solution to be inspected and a reagent. During the measurement, a reaction solution 5 obtained by making the sample solution react with the reagent is filled in the microchannel 4a. Since the absorbance of the reaction solution 5 varies depending on the ratio of the reaction between the sample solution and the reagent, variations in the amount of the light transmitted through the reaction solution 5 can be measured by irradiating the microchannel 4a with the transmitted light from a light source 6 and measuring the amount of the transmitted light in a light-reception part 7, whereby the reaction state can be analyzed.

While in this first embodiment the thicknesses of the substrate 1 and the substrate 2 are 1 mm to 5 mm, the thicknesses are not particularly restricted thereto so long as the microchannels 4a and 4b can be formed. Further, the shapes of the substrates 1 and 2 are also not particularly restricted, and the substrates may have any shape according to the application, such as disk, fan, sheet, plate, bar, or other complicated shapes.

While in this first embodiment plastic is used as a material of the substrates 1 and 2 in view of its high moldability, high productivity, and low price, the material of the substrates is not especially restricted thereto, and any material such as glass, silicon wafer, metal, or ceramic may be used so long as the substrates can be bonded together.

In this first embodiment, when the solution is transferred utilizing the capillary phenomenon on the substrate 1 having the microchannels 4a and 4b and the substrate 2, the microchannels 4a and 4b are subjected to a hydrophilic processing if necessary, whereby the viscosity resistance in the microchannels is reduced to facilitate the fluid migration.

Since the plastic material is used in this first embodiment, the hydrophilic processing is performed to the surface. However, a hydrophilic material such as glass may be used, or a hydrophilic agent such as a surface-activating agent, a hydrophilic polymer, or hydrophilic powders such as silica gel may be added to the material surface during molding to give a hydrophilicity to the surface. Further, methods of the hydrophilic processing may include a surface processing using an active gas such as plasma, corona, ozone, or fluorine, and a surface processing using a surface-activating agent. The hydrophilicity means that the contact angle with water is less than 90°, and more preferably, it is less than 40°.

While in this first embodiment the substrate 1 and the substrate 2 are bonded using an adhesive agent, these substrates 1 and 2 may be bonded by a bonding method such as fusion bonding or anodic bonding in accordance with the material to be used.

Figure 2:
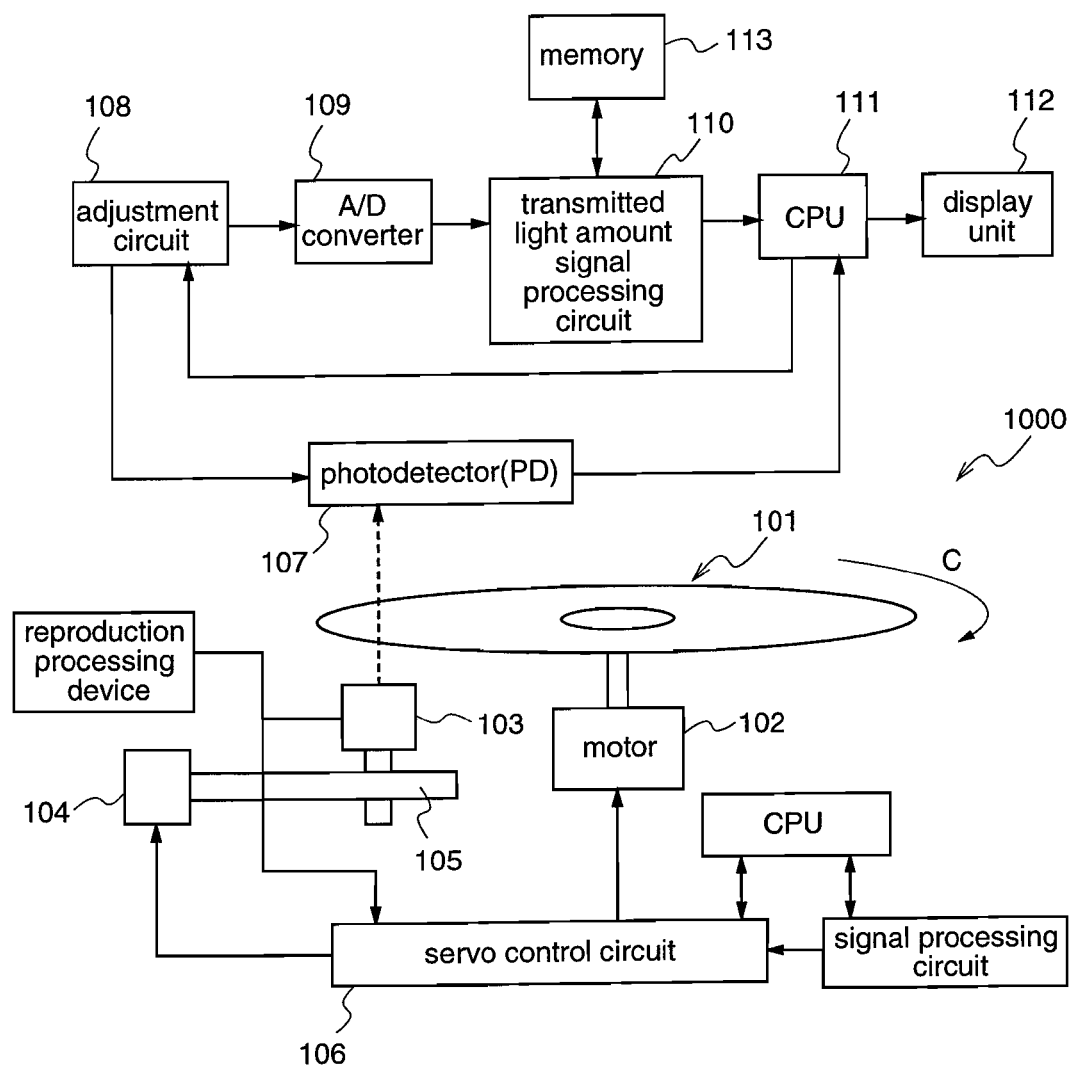
FIG. 2 is a diagram illustrating the construction of an analysis apparatus on which the analysis device 101 according to the first embodiment is mounted.

FIG. 2 is a schematic diagram illustrating the construction of an analysis apparatus on which the analysis device 101 according to the first embodiment is mounted.

In FIG. 2, the analysis device 101 according to the first embodiment is mounted on a motor 102 which is a rotation drive means of the analysis apparatus 1000, and the analysis device 101 is rotated around its axial center by driving the motor 102. The analysis device 101 can transfer and centrifugally separate the solution in the device by utilizing a centrifugal force caused by the rotation. While in this first embodiment a disk-shaped analysis device is loaded on the analysis apparatus, a plurality of analysis devices of a fan shape or other shapes may be simultaneously loaded.

Further, in the analysis apparatus 1000, laser light is emitted from a laser light source 103 toward the analysis device 101 while rotationally driving the analysis device 101 with the motor 102 in a C direction. The laser light source 103 is threadably mounted on a feed screw 105 that is driven by a traverse motor 104, and a servo control circuit 106 drives the traverse motor 104 to move the laser light source 103 radially such that the laser light source 103 can be located in an arbitrary measurement position.

Above the analysis device 101, there are provided a photodetector 107 for detecting the amount of light transmitted through the analysis device 101 out of the laser light emitted from the laser light source 103, a control circuit 108 for controlling the gain of the output from the photodetector 107, an A/D converter 109 for analog-to-digital converting the output of the control circuit 108, a transmitted light amount signal processing circuit 110 for processing the A/D converted data, a memory 113 for holding the data obtained in the transmitted light amount signal processing circuit 110, a CPU 111 for controlling the above-mentioned elements, and a display unit 112 for displaying the analysis result.

Next, a description will be given of the microchannel structure of the analysis device 101 according to the first embodiment, and the sample solution transfer process.

Figure 3:
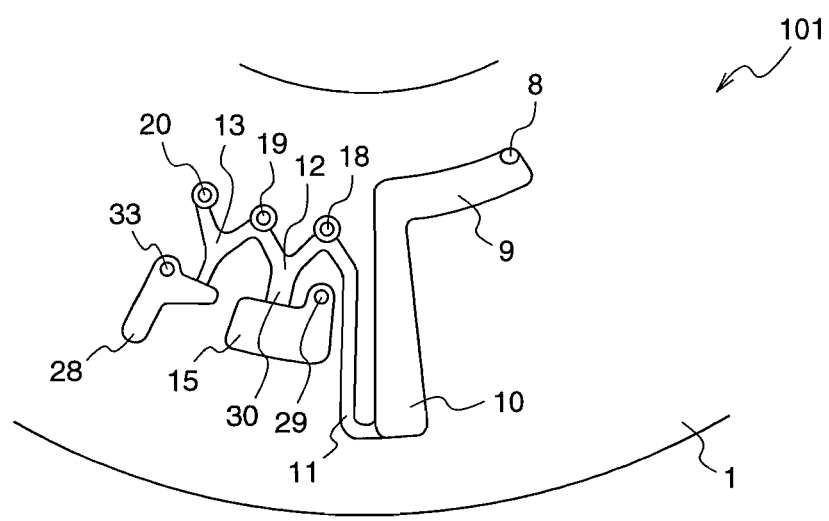
FIG. 3 is a plan view illustrating a microchannel structure of the analysis device 101 according to the first embodiment.
Figure 4A:
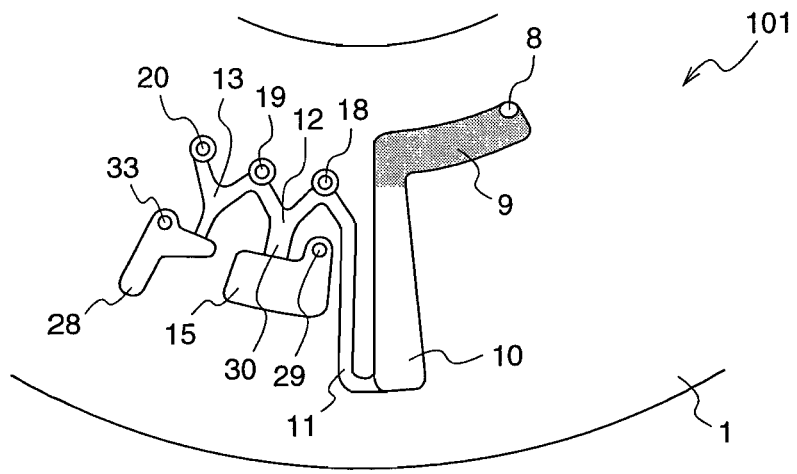
FIG. 4 is a diagram for explaining an injection/separation process of the analysis device 101 according to the first embodiment.
Figure 4B:
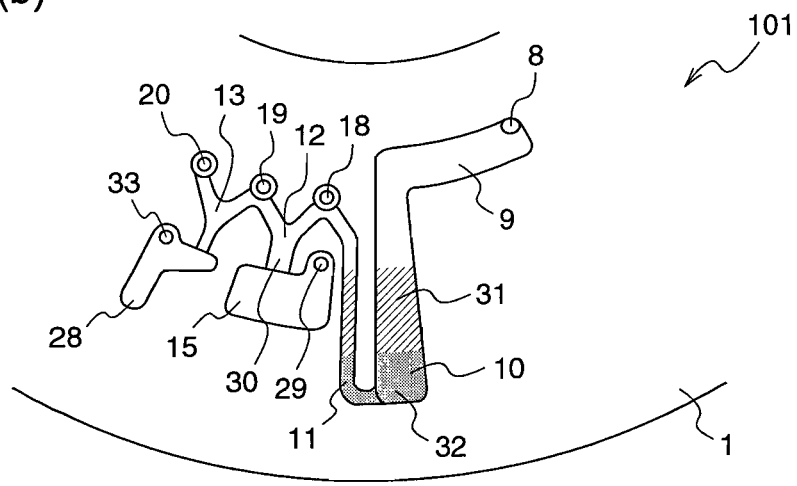
Figure 5A:
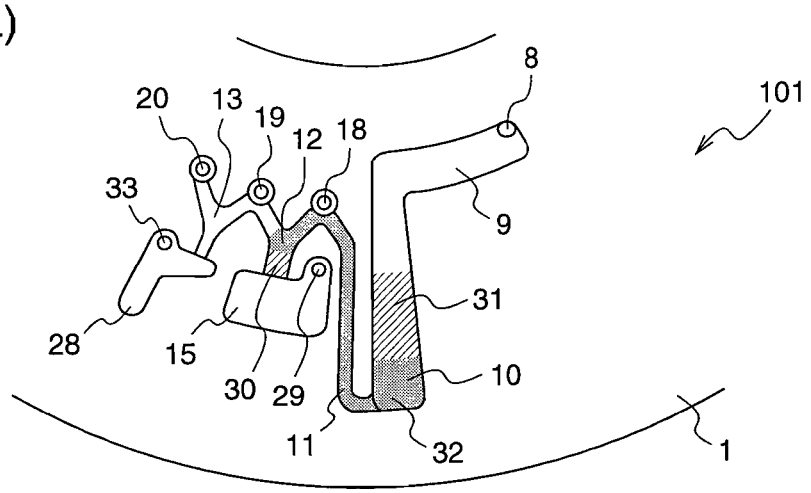
FIG. 5 is a diagram for explaining a measurement process and a measurement cell filling process of the analysis device 101 according to the first embodiment.
Figure 5B:
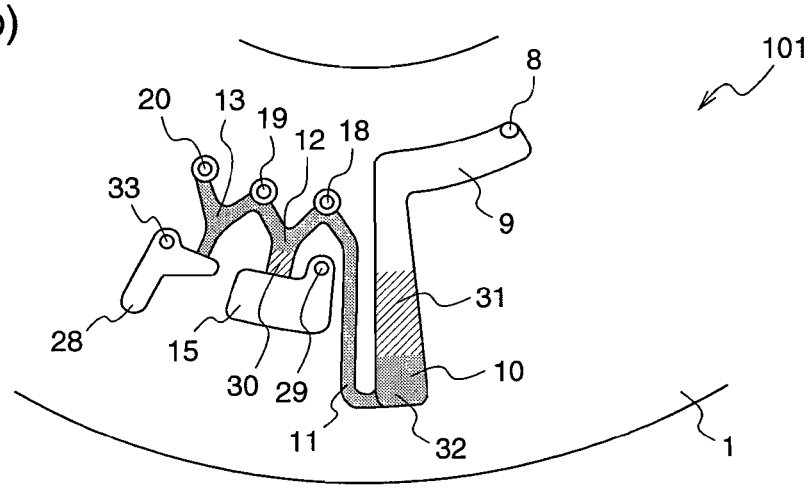
Figure 5C:
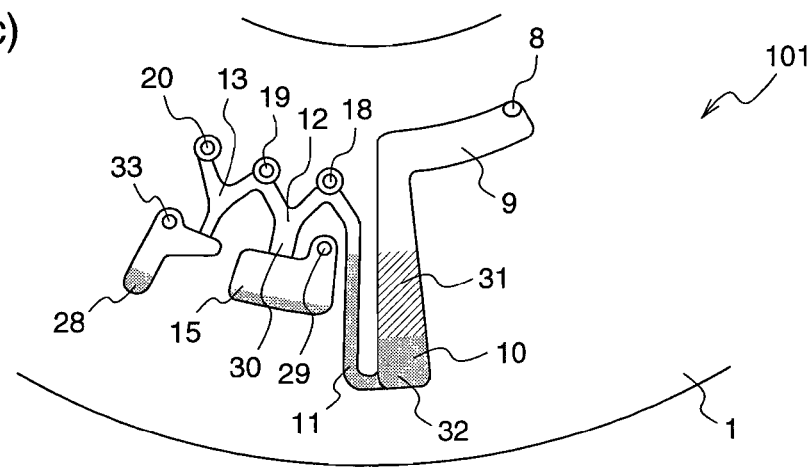

FIG. 3 is a plan view illustrating the microchannel structure of the analysis device 101 according to the first embodiment. FIGS. 4(a) and 4(b) are diagrams for explaining the injection/separation process of the analysis device 101, and FIGS. 5(a), 5(b), and 5(c) are diagrams for explaining the measurement process of the analysis device 101, and the measurement cell filling process.

With reference to FIGS. 3, 4, and 5, the microchannel structure of the analysis device 101 according to this first embodiment comprises a fluid storage chamber 9 in which a sample solution of an amount required for analysis is injected and stored, a separation chamber 10 for separating the sample solution into a solution component and a solid component by using a centrifugal force that is generated by rotation of the analysis device, a holding channel 13 to which a part of the solid component separated in the separation chamber 10 is transferred and stored, an overflow channel 12 which is disposed between the holding channel 13 and the separation chamber 10 and connected to the separation chamber 10 by a joint channel 11 for transferring the sample solution stored in the separation chamber 10, an overflow chamber 15 to which the sample solution filled in the overflow channel 12 is discharged, and a measurement cell 28 for holding the solid component filled in the holding channel 13, and mixing/reacting the solid component with a reagent to measure the absorbance, the turbidity, or the number of cells in the mixed solution.

In this first embodiment, a reagent to be reacted with the solid component is stored in the measurement cell 28. Further, a reagent reaction chamber for making the sample solution react with the reagent or an agitation chamber for performing agitation may be provided between the holding chamber 13 and the measurement cell 28 although they are omitted in the first embodiment.

While in this first embodiment the depths of the fluid storage chamber 9, the separation chamber 10, the overflow chamber 15, and the measurement cell 28 are 0.3 mm to 2 mm, the depths are adjustable according to the amount of the sample solution or the conditions for measuring the absorbance (the optical path length, the measurement wavelength, the reactive concentration of the sample solution, the kind of the reagent, etc.).

The fluid storage chamber 9 is connected to the separation chamber 10, and the sample solution of a previously measured amount is injected from an injection port 8 to be stored in the fluid storage chamber 9 as shown in FIG. 4(a) and then the analysis device 101 is rotated to generate a centrifugal force, whereby the sample solution can be transferred to the separation chamber 10 as shown in FIG. 4(b).

Further, in this first embodiment, a measurement function for making the separation chamber 10 hold a predetermined amount of the sample solution is not provided. However, in order to reduce the process steps prior to the sample solution injection, the separation chamber 10 may be provided with a measurement function for measuring the sample solution, such as a construction for, when the analysis device is rotated, discharging the excess solution into the overflow chamber through the overflow channel from the fluid surface position in the separation chamber at which the required amount of solution can be held, or a construction for providing a capillary channel communicating from the separation chamber to the outside of the analysis device, sucking the sample solution by a capillary force of the capillary channel, measuring the sample solution by the volume of the capillary channel, and transferring the sample solution in the capillary channel to the separation chamber by a centrifugal force.

While in this first embodiment the fluid storage chamber 9 and the separation chamber 10 are connected with the same depth, the separation chamber 10 may be provided with an air hole and the fluid storage chamber 9 and the separation chamber 10 may be connected by a capillary channel having a depth of 50 µm to 200 µm to prevent the sample solution from flowing into the separation chamber 10 during injection.

The separation chamber 10 is connected to the overflow channel 12 via the joint channel 11 from the radially outermost position of the separation chamber 10.

The joint channel 11 has a width of 0.5 mm to 2 mm and a depth of 50 µm to 200 µm, the width and depth of the joint channel 11 are not especially restricted thereto so long as the sample solution can be filled in the joint channel 11 by a capillary force that is generated when rotation of the analysis device 101 is stopped.

In the construction of the first embodiment, in order to prevent the sample solution from flowing out of the separation chamber 10 over the joint position of the joint channel 11 and the overflow channel 12 when the sample solution is transferred from the fluid storage chamber 9 to the separation chamber 10 by rotating the analysis device 101, it is necessary to optimize the size of the separation chamber 10, the joint position of the joint channel 11 and the overflow channel 12, and the like on the basis of the amount of the sample solution that has previously been measured. In this first embodiment, with respect to this point, the joint channel 11 is formed up to a position inner than the fluid surface obtained when the separation chamber 10 holds the predetermined amount of the sample solution, whereby the sample solution transferred from the fluid storage chamber 9 by the centrifugal force is held in the separation chamber 10 and in the joint channel 11 as shown in FIG. 4(b).

The sample solution stored in the separation chamber 10 can be separated into a solution component 31 and a solid component 32 as shown in FIG. 4(b) by rotating the analysis device 101 at a high speed for a few minutes. For example, when the sample solution is blood, the blood can be separated into blood plasma, and blood cells or high hematocrit blood (blood having a high ratio of blood cell component) by setting the rotation speed to 4000 rpm to 6000 rpm, and rotating the analysis device 101 for one to five minutes.

The separation chamber 10 is connected to the holding channel 13 through the joint channel 11 and the overflow channel 12, and the overflow channel 12 is connected to the overflow chamber 15 that is positioned outer than the overflow channel 12, and the holding channel 13 is connected to the measurement cell 28 that is positioned outer than the holding channel 13.

The depths of the holding channel 13 and the overflow channel 12 are 50 µm to 200 µm. When the rotation of the analysis device 101 is stopped, the separated solid component or high-density solid component solution in the separation chamber 10 is filled in the holding channel 13 and the overflow channel 12 by the capillary force.

At this time, although all of the solution component 31 separated in the joint channel 11 is initially transferred to the overflow channel 12 by the capillary force, since the overflow chamber 15 is formed deep, the solution component 31 is not transferred into the overflow chamber 15 but stored in the junction part 30 between the overflow channel 12 and the overflow chamber 15. Thereafter, the solid component 32 that is separated between the joint channel 11 and the separation chamber 10 is transferred to the holding channel 13 through the overflow channel 12.

In the construction of the first embodiment, since the solution component 31 exists at the inner circumference part of the joint chamber 11 that connects the overflow channel 12 and the separation chamber 10 as shown in FIG. 4(b) when the sample solution is subjected to centrifugal separation in the separation chamber 10, if the solution component 31 flows into the holding channel 13 as it is, the concentration of the solid component is reduced, which causes variations in the measurement precision. So, in this first embodiment, as shown in FIG. 5(a), at the branching point between the overflow channel 12 and the holding channel 13, the opening area of the overflow channel 12 in the junction part 30 between the overflow channel 12 and the overflow chamber 15 is made larger than the opening area of the holding channel 13, thereby to make the solution component 31 flow into the overflow channel 12 with priority. The ratio of the opening area of the overflow channel 12 to that of the holding channel 13 is desired to be 1.5 to 5 times. When the ratio is smaller than 1.5 times, the solution component 31 might flow into the holding channel 13. When it is larger than 5 times, since the area of the overflow channel 12 becomes too large, the solid component 32 is filled in the overflow channel 12 beyond necessity, which may results in an increase in the loss of the solid component 32.

In this first embodiment, the overflow channel 12 is provided between the joint channel 11 and the holding channel 13, and further, the opening areas of these two channels at the branching point between the holding channel 13 and the overflow channel 12 are constituted such that the opening area of the overflow channel 12 is larger than the opening area of the holding channel 13, whereby the solution component 31 can be transferred into the overflow channel 12 with priority relative to the holding channel 13. However, it is also possible to provide the overflow channel 12 from the joint channel 11 via the holding channel 13.

Since the holding channel 13 and the overflow channel 12 can measure the solution by their volumes, the allowable volumes of the respective channels for holding the solid component 32 are determined by adjusting the opening areas of the holding channel 13 and the overflow channel 12 having the predetermined depth, and thereby each channel can hold the desired amount of solution. That is, the solution component 31 is prevented from flowing into the holding channel 13 by designing the allowable volume of the overflow channel 12 such that all of the solution component 31 existing in the joint channel 11 can be stored in the overflow channel 12, and the solid component 32 of an amount at least 0.5 time as large as the stored solution component 31 can flow into the overflow channel 12.

By rotating the analysis device 101 to apply a centrifugal force, air is introduced from the air hole 19 and a pressure is applied to the boundary between the holding channel 13 and the overflow channel 12, and thereby the continuous solution filled in the holding channel 13 is separated at the position of the air hole 19, i.e., at the boundary of the holding channel 13 and the overflow channel 12, and then the solution filled in the space between the air hole 19 and the air hole 20 flows into the measurement cell 28.

Likewise, the solution filled in the overflow channel 12 is also broken at the position between the air hole 10 and the air hole 19, and the solution filled in the space between the position of the air hole 18 and the position of the air hole 19 flows into the overflow chamber 15, while the solution filled in the space between the position of the air hole 18 and separation chamber 10 is returned to the separation chamber 10 by the centrifugal force.

After the holding channel 13 is filled up as shown in FIG. 5(b), the analysis device 101 is rotated again, and thereby the solid component stored in the holding channel 13 is transferred to the measurement cell 28 by a centrifugal force, while the sample solution filled in the overflow channel 12 is transferred to the overflow chamber 15 as shown in FIG. 5(c).

While the solid component that flows into the measurement cell 28 is mixed with the reagent held in the measurement cell 28 by acceleration/deceleration of rotation or diffusion of the solution when the rotation is stopped, this mixing may be performed by using an external force such as vibration.

As for the analysis target component which is included in the solid component mixed with the reagent in the measurement cell 28, its concentration in the sample solution can be calculated by measuring its reaction state with the reagent in absorbance measurement or the like.

According to the analysis device 101 and the analysis apparatus 1000 of the first embodiment, the analysis device in which a sample solution to be analyzed is stored and the sample solution can be transferred comprises the separation chamber 10 for separating the sample solution into a solution component and a solid component by using a centrifugal force that is generated by rotation of the analysis device, the holding channel 13 to which a part of the solid component separated in the separation chamber is transferred and stored, and the overflow channel 12 which is disposed between the holding channel and the separation chamber and connected to a joint channel for transferring the sample solution stored in the separation chamber, and the analysis device 101 is constituted such that, after the solution component that is separated in the separation chamber and exists in the joint channel flows into the overflow channel with priority, the solid component separated in the separation chamber is filled in the overflow channel via the joint channel, and then the solid component in the separation chamber flows into the holding channel from the joint channel via the overflow channel so that a part of the solid component is held in the holding channel. Furthermore, the analysis device includes the overflow chamber 15 to which the sample solution filled in the overflow channel is discharged, and the analysis device is constituted such that the overflow chamber is connected to the overflow channel via the junction part 30, and transfer of the sample solution from the joint channel to the overflow channel is performed by a capillary force with the opening area of the overflow channel at the junction part between the overflow channel and the overflow chamber being larger than that of the holding channel. By making the opening area of the overflow channel larger than the opening area of the holding channel, the solution component can be introduced and discharged into the overflow channel with priority relative to the holding channel. Further, by adjusting the opening areas of the holding channel and the overflow channel, the allowable volumes to be held by the respective channels can be determined, and thereby the solid component or the high-concentration solid component solution obtained by performing the centrifugal operation can be transferred by a required amount to the holding channel, resulting in enhanced measurement precision of the analysis device.

[Embodiment 2]

Hereinafter, an analysis device 201 according to a second embodiment and an analysis apparatus 1000 using the analysis device 201 will be described with reference to FIGS. 6 to 8.

The main construction of the analysis device 201 and the construction of the analysis apparatus 1000 on which the analysis device 201 is mounted are identical to those of the first embodiment, and therefore, repeated description is not necessary.

Figure 6:
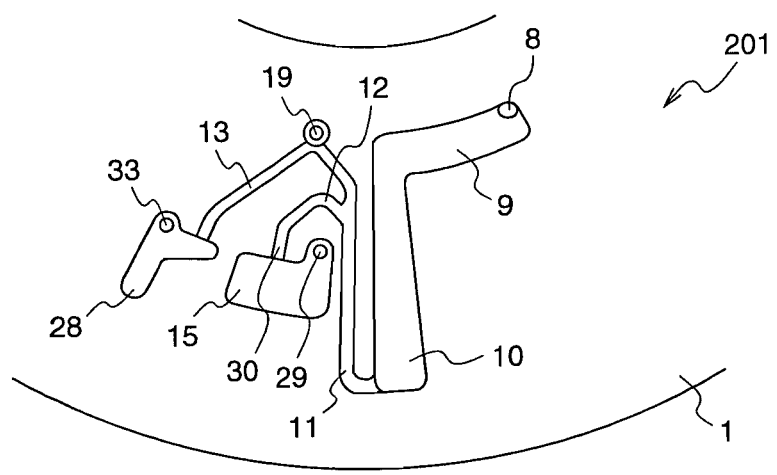
FIG. 6 is a plan view illustrating a microchannel structure of an analysis device 201 according to a second embodiment of the present invention.
Figure 7A:
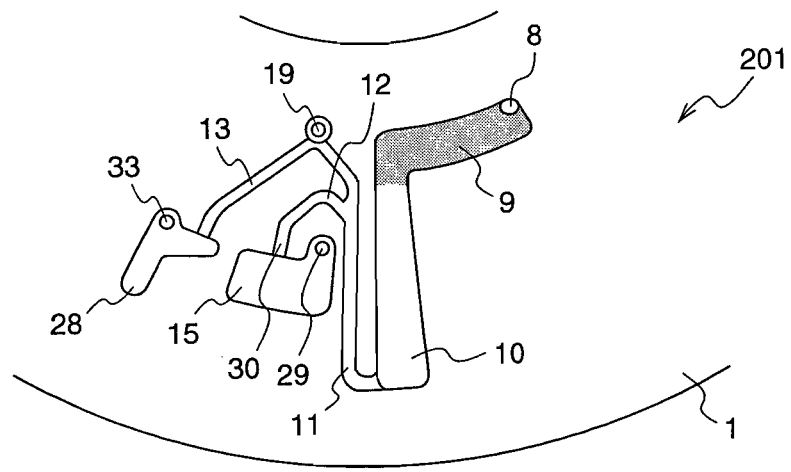
FIG. 7 is a diagram for explaining an injection/separation process of the analysis device 201 according to the second embodiment.
Figure 7B:
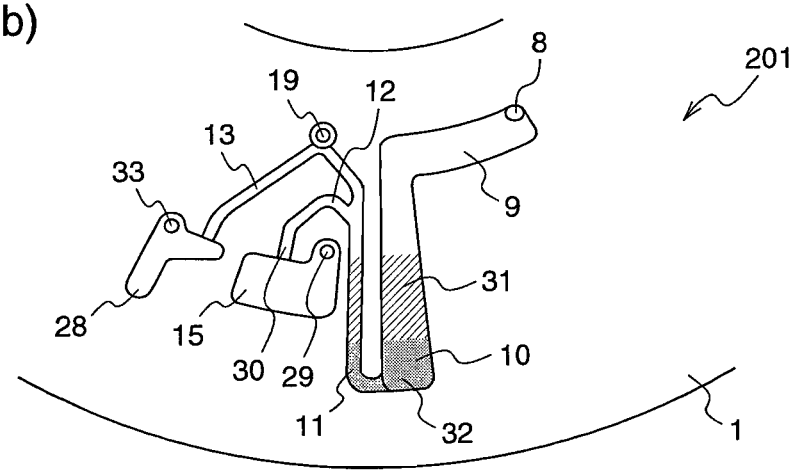
Figure 8A:
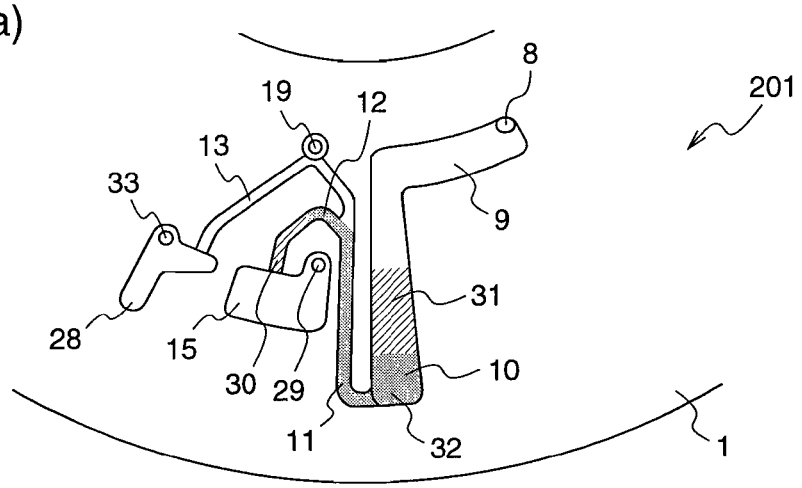
FIG. 8 is a diagram for explaining a measurement process and a measurement cell filling process of the analysis device 201 according to the second embodiment.
Figure 8B:
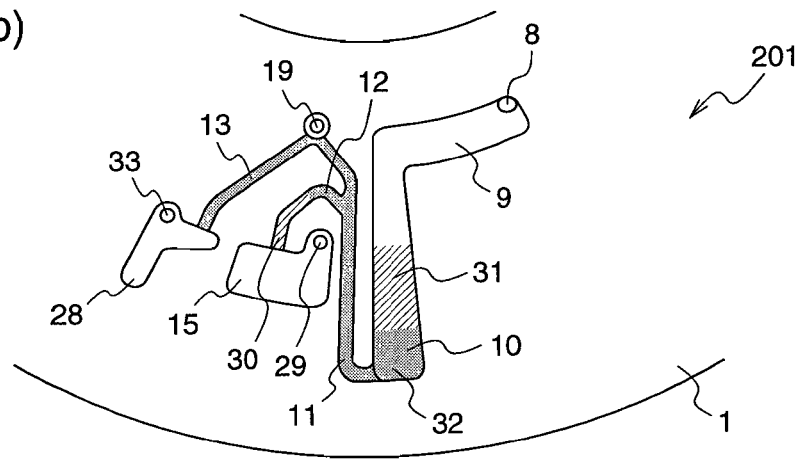
Figure 8C:
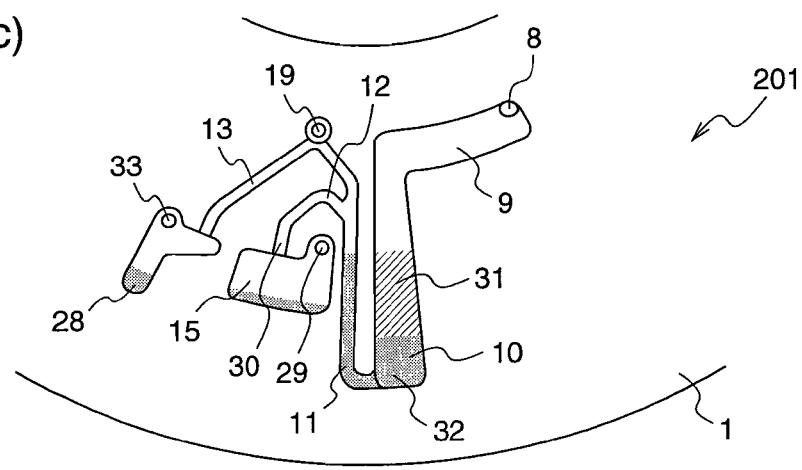

FIG. 6 is a plan view illustrating the structure of microchannels in the analysis device 201 of the second embodiment. FIGS. 7(a) and 7(b) are diagrams for explaining the injection and separation processes of the analysis device 201, and FIGS. 8(a), 8(b), and 8(c) are diagrams for explaining the measurement process of the analysis device 201 and the filling process of the measurement cell 28.

With reference to FIGS. 6, 7, and 8, the microchannel structure of the analysis device 201 according to the second embodiment comprises a fluid storage chamber 9 in which a sample solution of an amount required for analysis is injected and stored, a separation chamber 10 for separating the sample solution into a solution component and a solid component by using a centrifugal force that is generated by rotation of the analysis device 201, a holding channel 13 to which a part of the solid component separated in the separation chamber 10 is transferred to be stored, an overflow channel 12 which is connected to the holding channel 13 and the separation chamber 10 via a joint channel 11 for transferring the sample solution in the separation chamber 10, an overflow chamber 15 into which the sample solution filled in the overflow channel 12 is discharged, and a measurement cell 28 for holding the solid component filled in the holding channel 13, and mixing and reacting the solid component with a reagent to measure the absorbance, the turbidity, or the number of cells in the mixed solution.

In this second embodiment, the reagent to be reacted with the solid component is held in the measurement cell 28. Further, a reagent reaction chamber for making the sample solution react with the reagent and an agitation chamber for performing agitation may be provided between the holding chamber 13 and the measurement cell 28 although they are omitted in this second embodiment.

While in this second embodiment the depths of the fluid storage chamber 9, the separation chamber 10, the overflow chamber 15, and the measurement cell 28 are 0.3 mm to 2 mm, these depths are adjustable in accordance with the amount of the sample solution or the conditions for absorbance measurement (the optical path length, the measurement wavelength, the reaction concentration of the sample solution, the kind of the reagent, etc.).

The fluid storage chamber 9 is connected to the separation chamber 10, and a previously measured amount of the sample solution is injected from an injection port 8 and stored in the fluid storage chamber 9 as shown in FIG. 7(a), and then the analysis device 201 is rotated to generate a centrifugal force, whereby the sample solution can be transferred to the separation chamber 10 as shown in FIG. 7(b).

Further, in this second embodiment, a measurement function for making the separation chamber 10 hold a predetermined amount of the sample solution is not provided. However, in order to reduce the process steps before injection of the sample solution, the separation chamber 10 may be provided with a measurement function for measuring the amount of the sample solution, such as a construction for, when the analysis device is rotated, discharging the excess solution into the overflow chamber through the overflow channel from the fluid surface position in the separation chamber at which the required amount of solution can be held, or a construction for providing a capillary channel communicating from the separation chamber to the outside of the analysis device, sucking the sample solution by a capillary force of the capillary channel, measuring the sample solution by the volume of the capillary channel, and transferring the sample solution in the capillary channel to the separation chamber by a centrifugal force.

While in this second embodiment the fluid storage chamber 9 and the separation chamber 10 are connected with the same depth, the separation chamber 10 may be provided with an air hole and the fluid storage chamber 9 and the separation chamber 10 may be connected by a capillary channel having a depth of 50 µm to 200 µm to prevent the sample solution from flowing into the separation chamber 10 during injection.

The separation chamber 10 is connected to the overflow channel 12 and the holding channel 13 via the joint channel 11 from the radially outermost position of the separation chamber 10.

The joint channel 11 has a width of 0.5 mm to 2 mm and a depth of 50 µm to 200 µm, the width and depth are not especially restricted thereto.

In the construction of the second embodiment, in order to prevent the sample solution from flowing out of the separation chamber 10 beyond the joint position of the joint channel 11 and the overflow channel 12 when the sample solution is transferred from the fluid storage chamber 9 to the separation chamber 10 by rotating the analysis device 201, it is necessary to optimize the size of the separation chamber, the joint position of the joint channel 11 and the overflow channel 12 and the like on the basis of the amount of the sample solution that has previously been measured. In this second embodiment, with respect to this point, the joint channel 11 is formed up to a position inner than the fluid surface obtained when the separation chamber 10 holds the predetermined amount of the sample solution, and therefore, the sample solution transferred from the fluid storage chamber 9 by the centrifugal force is held in the separation chamber 10 and the joint channel 11 as shown in FIG. 7(b).

The sample solution held in the separation chamber 10 can be separated into a solution component 31 and a solid component 32 as shown in FIG. 7(b) by rotating the analysis device at a high speed for a few minutes. For example, when the sample solution is blood, the blood can be separated into blood plasma and blood cells or high hematocrit blood (blood having a high ratio of blood cell component) by setting the rotation speed at 4000 rpm to 6000 rpm and performing the rotation for one to five minutes.

The overflow channel 12 is connected to the overflow chamber 15 that is positioned outer than the overflow channel 12, and the holding channel 13 is connected to the measurement cell 28 that is positioned outer than the holding channel 13.

The depths of the holding channel 13 and the overflow channel 12 are 50 µm to 200 µm, and filling of the solution into the holding channel 13 and the overflow channel 12 is performed by a suction force.

In the construction according to the second embodiment, since the solution component 31 exists at the inner circumference part of the joint channel 11 connecting the overflow channel 12 and the separation chamber 10 when the sample solution is centrifugally separated in the separation chamber 10 as shown in FIG. 7(b), if the solution component 31 flows into the holding channel 13 as it is, the concentration of the solid component is reduced, which causes variations in measurement precision. So, in this second embodiment, as shown in FIG. 8(a), an air hole 29 provided on the overflow chamber 15 is connected to a suction pump (not shown) by a connection means such as a tube (not shown), and air in the overflow channel 12 and the joint channel 11 is sucked by driving the suction pump, and the solution component 31 existing in the joint channel 11 is transferred with priority to the junction part 30 of the overflow channel 12 and the overflow channel 15 by a pressure difference caused by the suction. Thereafter, the suction pump is connected to an air hole 33 provided on the measurement cell 28 by a connection means such as a tube, and air is similarly sucked from the air hole 33, whereby the solid component 32 in the separation chamber 10 can be filled in the holding channel 13. Preferably, the air hole 19 and the air hole 29 are hermetically sealed.

Since the holding channel 13 and the overflow channel 12 can measure the solution by their volumes, the allowable volume of the solid component 32 is determined by adjusting the opening areas of the holding channel 13 and the overflow channel 12 having the predetermined depth, and thereby each channel can hold a required amount of solution. That is, the solution component 31 is prevented from flowing into the holding channel 13 by designing the allowable volume of the overflow channel 12 such that all of the solution component 31 existing in the joint channel 11 can be stored in the overflow channel 12, and the solid component 32 of an amount at least 0.5 time as large as the stored solution component 31 can flow into the overflow channel 12.

By rotating the analysis device 201 to generate a centrifugal force, air is introduced from the air hole 19 and a pressure is applied to the boundary between the holding channel 13 and the overflow channel 12, and thereby the continuous solution filled in the holding channel 13 is separated at the position of the air hole 19, i.e., at the boundary of the holding channel 13 and the overflow channel 12, and then the solution filled in the space between the air hole 19 and the air hole 20 flows into the measurement cell 28.

Likewise, the solution filled in the overflow channel 12 is also broken at the position of the air hole 19, and the solution filled in the space between the position of the air hole 19 and the overflow chamber 15 flows into the overflow chamber 15, while the solution filled in the space between the position of the air hole 19 and the separation chamber 10 is returned into the separation chamber 10 by the centrifugal force.

After the holding channel 13 is filled as shown in FIG. 8(b), the analysis device 201 is rotated again, whereby the solid component held in the holding channel 13 is transferred to the measurement cell 28 by a centrifugal force, while the sample solution filled in the overflow channel 12 is transferred to the overflow chamber 15.

Although the solid component that flows into the measurement cell 28 is mixed with the reagent held in the measurement cell 28 due to acceleration/deceleration of rotation or diffusion of the solution while the rotation is stopped, this mixing may be performed using an external force such as vibration.

As for the analysis target component which is included in the solid component mixed with the reagent in the measurement cell 28, its concentration in the sample solution can be calculated by measuring its reaction state with the reagent in absorbance measurement or the like.

According to the analysis device 201 of the second embodiment and the analysis apparatus 1000 using the analysis device 201, the analysis device is provided with the separation chamber 10 for separating the sample solution into a solution component and a solid component by using a centrifugal force that is generated due to rotation of the analysis device, the holding channel 13 to which a part of the solid component separated in the separation chamber is transferred and stored, and the overflow channel 12 which is connected to the holding channel and the separation chamber via the joint channel for transferring the sample solution in the separation chamber, and the analysis device 201 is constituted such that, after the solution component 31 that is separated in the separation chamber and exists in the joint channel flows into the overflow channel with priority, the solid component 32 separated in the separation chamber is introduced into the overflow channel via the joint channel, and then the solid component in the separation chamber flows into the holding channel from the joint channel via the overflow channel so that a part of the solid component is held in the holding channel. Further, the analysis device further includes the overflow chamber 15 to which the sample solution filled in the overflow channel is discharged, and the overflow chamber is connected to the overflow channel via the junction part 30, and transfer of the sample solution from the joint channel to the overflow channel is performed such that air in the overflow channel and the joint channel is sucked from the air hole 29 provided on the overflow chamber by a suction pump, and the solution component existing in the joint channel is transferred with priority to the junction part between the overflow channel and the overflow chamber due to a pressure difference caused by the suction, whereby the solution component existing in the joint channel can be discharged. Furthermore, by adjusting the opening areas of the holding channel and the overflow channel, the allowable volumes to be held by the respective channels can be determined, and thereby the solid component or the high-concentration solid component solution obtained by performing the centrifugal operation can be transferred by a requires amount, resulting in enhanced measurement precision of the analysis device.

[Embodiment 3]

Hereinafter, an analysis device 301 according to a third embodiment corresponding to claims 6, 7, 9, and 10 and an analysis apparatus 1000 using the analysis device 301 will be described with reference to FIGS. 9 to 11.

The main construction of the analysis device 301 and the construction of the analysis apparatus 1000 on which the analysis device 301 is mounted are identical to those of the first embodiment, and therefore, repeated description is not necessary.

Figure 9:
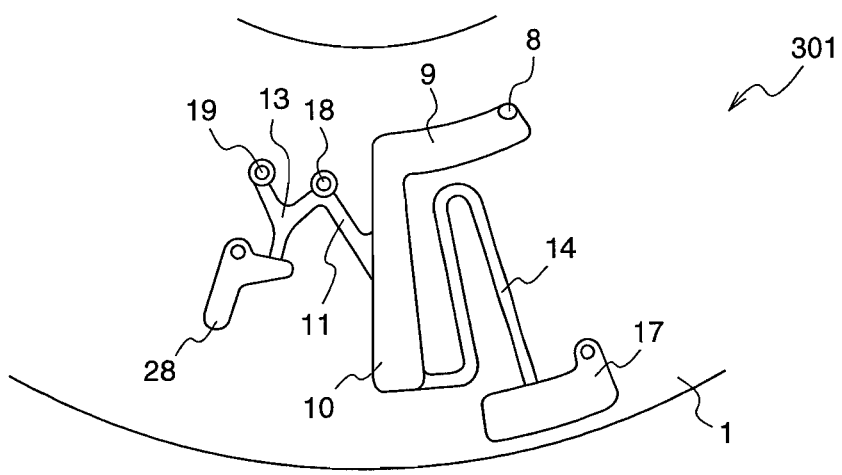
FIG. 9 is a plan view illustrating a microchannel structure of an analysis device 301 according to a third embodiment of the present invention.
Figure 10A:
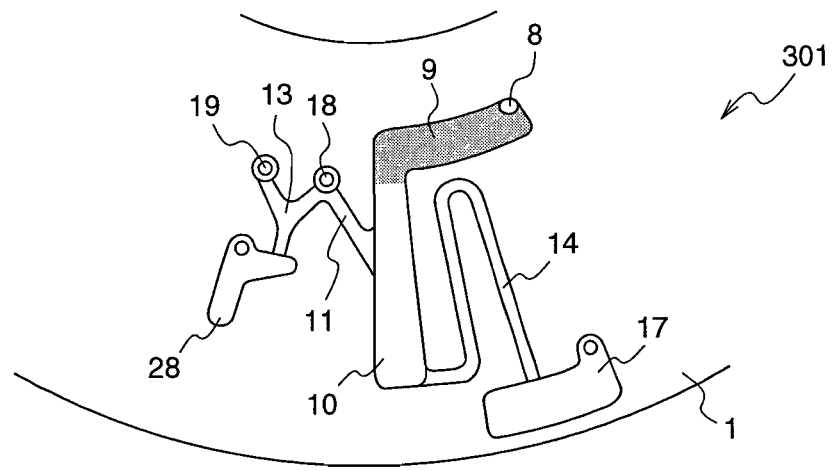
FIG. 10 is a diagram for explaining an injection/separation process of the analysis device 301 according to the third embodiment.
Figure 10B:
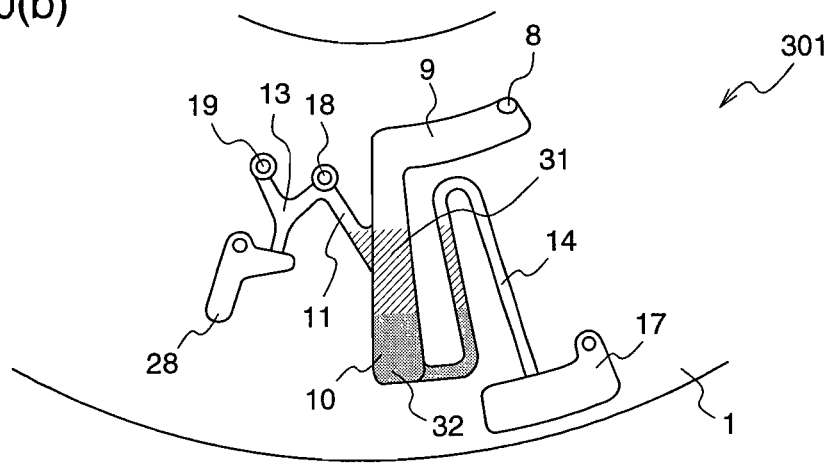
Figure 11A:
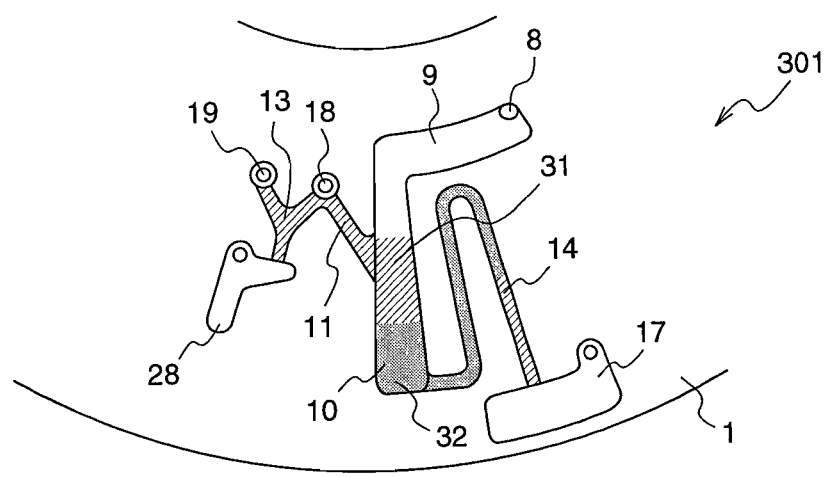
FIG. 11 is a diagram for explaining a measurement process and a measurement cell filling process of the analysis device 301 according to the third embodiment.
Figure 11B:
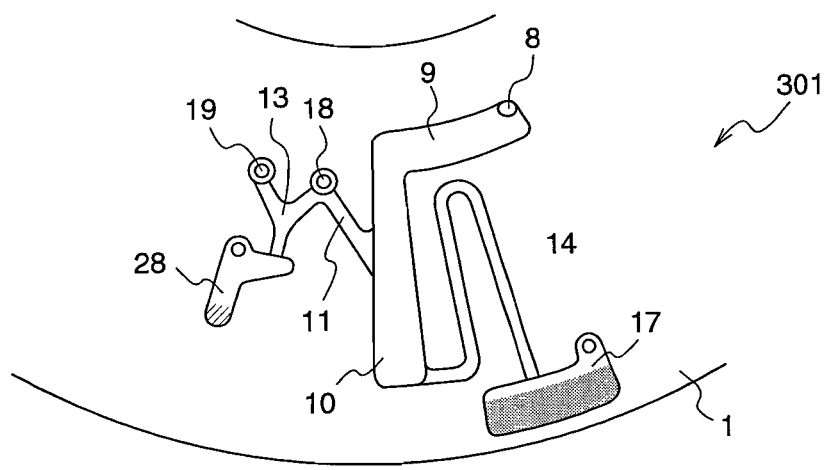

FIG. 9 is a plan view illustrating a microchannel structure in the analysis device 301 of the third embodiment. FIGS. 10(a) and 10(b) are diagrams for explaining the injection/separation processes of the analysis device 301, and FIGS. 11(a) and 11(b) are diagrams for explaining the measurement process of the analysis device 301 and the filling process of the measurement cell 28.

With reference to FIG. 9, the microchannel structure of the analysis device 301 according to the third embodiment comprises a fluid storage chamber 9 in which a sample solution of an amount required for analysis is injected and stored, a separation chamber 10 for separating the sample solution into a solution component and a solid component by using a centrifugal force that is generated by rotation of the analysis device 301, a holding channel 13 to which a part of the solid component separated in the separation chamber 10 is transferred to be stored, a sample overflow chamber 17 for discharging the sample solution remaining in the separation chamber 10, a joint channel 14 for connecting the separation chamber 10 and the sample overflow chamber 17, and a measurement cell 28 for holding the solid component filled in the holding channel 13, and mixing and reacting the solid component with a reagent to measure the absorbance or the turbidity of the mixed solution.

In this third embodiment, the reagent to be reacted with the solid component is held in the measurement cell 28. Further, a reagent reaction chamber for making the sample solution react with the reagent and an agitation chamber for performing agitation may be provided between the holding chamber 13 and the measurement cell 28 although they are omitted in this third embodiment.

While in this third embodiment the depths of the fluid storage chamber 9, the separation chamber 10, the sample overflow chamber 17, and the measurement cell 28 are 0.3 mm to 2 mm, these depths are adjustable according to the amount of the sample solution or the conditions for absorbance measurement (the optical path length, the measurement wavelength, the reaction concentration of the sample solution, the kind of the reagent, etc.).

The fluid storage chamber 9 is connected to the separation chamber 10, and a previously measured amount of the sample solution is injected from the injection port 8 and stored in the fluid storage chamber 9 as shown in FIG. 10(a), and then the analysis device 301 is rotated to generate a centrifugal force, whereby the sample solution can be transferred to the separation chamber 10 as shown in FIG. 10(b).

In this third embodiment, a measurement function for making the separation chamber 10 hold a predetermined amount of the sample solution is not provided. However, in order to reduce the process steps before injection of the sample solution, the separation chamber 10 may be provided with a measurement function for measuring the amount of the sample solution, such as a construction for, when the analysis device is rotated, discharging the excess solution into the overflow chamber through the overflow channel from the fluid surface position in the separation chamber at which the required amount of solution can be held, or a construction for providing a capillary channel communicating from the separation chamber to the outside of the analysis device, sucking the sample solution by a capillary force of the capillary channel, measuring the sample solution by the volume of the capillary channel, and transferring the sample solution in the capillary channel to the separation chamber by a centrifugal force.

While in this third embodiment the fluid storage chamber 9 and the separation chamber 10 are connected with the same depth, the separation chamber 10 may have an air hole and the fluid storage chamber 9 and the separation chamber 10 may be connected by a capillary channel having a depth of 50 μm to 200 μm to prevent the sample solution from flowing into the separation chamber 10 during injection.

The separation chamber 10 is connected to the holding channel 13 via the joint channel 11 from the position where the separated solution component of the sample solution exists, and further, it is connected to the sample overflow chamber 17 via the joint channel 14 having a siphon shape at a position outer than the radially outermost position of the separation chamber 10.

The joint channel 11 and the joint channel 14 have the widths of 0.5 mm to 2 mm and the depths of 50 μm to 200 μm, the widths and depths are not especially restricted thereto so long as the joint channel 11 and the joint channel 14 can be filled with the sample solution by a capillary force that is generated when the rotation of the analysis device is stopped.

In the construction of the third embodiment, in order to prevent the sample solution from flowing out of the separation chamber 10 beyond the joint position of the joint channel 11 and the holding channel 13 and the curved point of the siphon of the joint channel 14 when the sample solution is transferred from the fluid storage chamber 9 to the separation chamber 10 by rotating the analysis device 301, it is necessary to optimize the size of the separation chamber 10, the joint position of the joint channel 11 and the holding channel 13, the position of the curved point of the siphon of the joint channel 14, and the like on the basis of the amount of the sample solution which has previously been measured. For this purpose, in this third embodiment, the joint channel 11 is formed up to a position inner than the fluid surface obtained when the separation chamber 10 holds the predetermined amount of the sample solution, and the joint channel 14 has the curved point of the siphon at a position inner than the fluid surface obtained when the separation chamber 10 holds the predetermined amount of the sample solution, whereby the sample solution transferred from the fluid storage chamber 9 by the centrifugal force is held in the separation chamber 10 and the joint channels 11 and 14 as shown in FIG. 10(b).

The sample solution held in the separation chamber 10 can be separated into a solution component 31 and a solid component 32 as shown in FIG. 10(b) by rotating the analysis device at a high speed for a few minutes. For example, when the sample solution is blood, the blood can be separated into blood plasma and blood cells or high hematocrit blood (blood having a high ratio of blood cell component) by setting the rotation speed at 4000 rpm to 6000 rpm, and performing the rotation for one to five minutes.

The separation chamber 10 is connected to the holding channel 13 via the joint channel 11, and the holding channel 13 is connected to the measurement cell 28 that is positioned outer than the holding channel 13.

The depth of the holding channel 13 is 50 μm to 200 μm, and the separated solution component in the separation chamber 10 is filled in the holding channel 13 by a capillary force when the rotation of the analysis device 301 is stopped.

Since the holding channel 13 can measure the solution by its volume, the allowable volume of the solution component 31 is determined by adjusting the opening area of the holding channel 13 having the predetermined depth, and the holding channel 13 can hold a desired amount of the solution.

By rotating the analysis device 301 to generate a centrifugal force, air is introduced from the air hole 18 and a pressure is applied to the boundary of the holding channel 13 and the joint channel 11, and thereby the continuous solution filled in the holding channel 13 is broken at the position of the air hole 18, i.e., at the boundary of the holding channel 13 and the joint channel 11, and then the solution filled in the space between the air hole 18 and the air hole 19 flows into the measurement cell 28.

After the holding channel 13 is filled as shown in FIG. 11(a), the analysis device 301 is rotated again, whereby the solution component held in the holding channel 13 is transferred to the measurement cell 28 by a centrifugal force as shown in FIG. 11(b).

In this third embodiment, the sample solution in the separation chamber 10 is discharged to the sample overflow chamber 17 by the siphon effect of the joint channel 14, in order to prevent the sample solution remaining in the separation chamber 10 from flowing into the holding channel 13 by a capillary force when the rotation of the analysis device 301 is stopped after the solution in the holding channel 13 is transferred to the measurement cell 28 and again flowing into the measurement cell 28 during the next rotation, which causes a change in the mixing ratio of the solution in the measurement cell 28.

Although the solution component that flows into the measurement cell 28 is mixed with the reagent held in the measurement cell 28 due to acceleration/deceleration of rotation or diffusion of the solution while the rotation is stopped, this mixing may be performed using an external force such as vibration.

As for the analysis target component which is included in the solution component mixed with the reagent in the measurement cell 28, its concentration in the sample solution can be calculated by measuring its reaction state with the reagent in absorbance measurement or the like.

According to the analysis device 301 of the third embodiment and the analysis apparatus 1000 using the analysis device 301, the analysis device 301 is provided with the fluid storage chamber 9 for holding the sample solution, the holding channel 13 which is connected to the solution storage chamber and holds a part of the sample solution that is transferred from the fluid storage chamber by a capillary force, the fluid holding chamber (measurement cell) 28 for holding the sample solution stored in the holding channel, which is transferred by a centrifugal force caused by rotation of the analysis device, and the sample overflow chamber 17 which is connected to the fluid storage chamber via the capillary channel 14 having the siphon structure, and positioned outer than the fluid storage chamber with respect to the axis center of the analysis device when the analysis device is rotated around the axis center. Therefore, the solution component obtained by performing the centrifugal separation can be transferred by a required amount. Further, the sample solution that remains when a part of the sample solution has been transferred can be prevented from flowing in afterward, thereby enhancing the measurement precision of the analysis device.

[Embodiment 4]

Hereinafter, an analysis device 401 according to a fourth embodiment corresponding to claims 6, 8, 9, and 10 and an analysis apparatus 1000 using the analysis device 401 will be described with reference to FIGS. 12 to 14.

The main construction of the analysis device 401 and the construction of the analysis apparatus 1000 on which the analysis device 401 is mounted are identical to those described for the first embodiment, and therefore, repeated description is not necessary.

Figure 12:
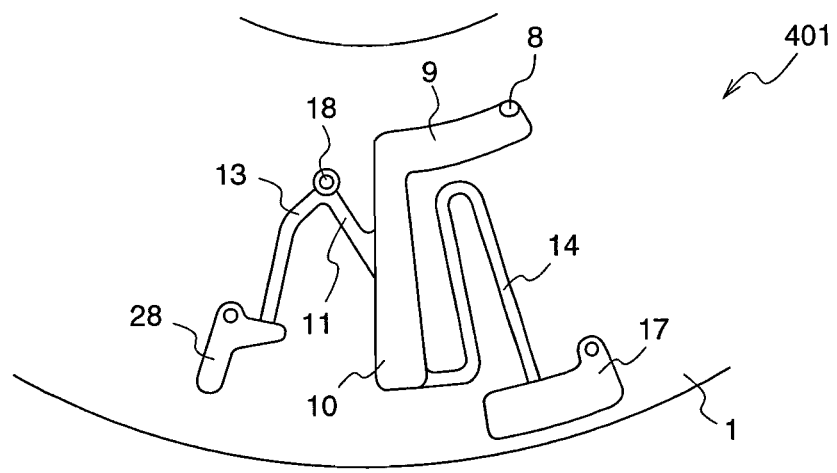
FIG. 12 is a plan view illustrating a microchannel structure of an analysis device 401 according to a fourth embodiment of the present invention.
Figure 13A:
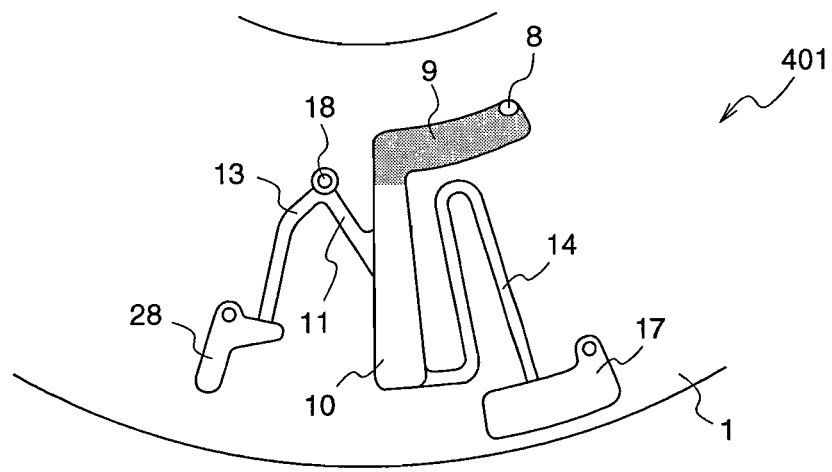
FIG. 13 is a diagram for explaining an injection/separation process of the analysis device 401 according to the fourth embodiment.
Figure 13B:
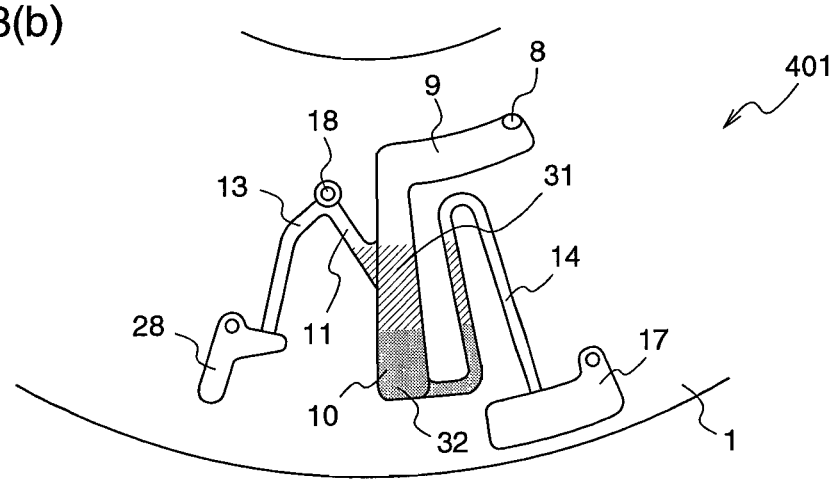

FIG. 12 is a plan view illustrating a microchannel structure in the analysis device 401 of the fourth embodiment. FIGS. 13(a) and 13(b) are diagrams for explaining the injection/separation processes of the analysis device 401, and FIGS. 14

(a) and 14 (b) are diagrams for explaining the measurement process and the measurement cell filling process of the analysis device 401.

With reference to FIG. 12, the microchannel structure of the analysis device 401 according to the fourth embodiment comprises a fluid storage chamber 9 in which a sample solution of an amount required for analysis is injected and stored, a separation chamber 10 for separating the sample solution into a solution component and a solid component by using a centrifugal force that is generated by rotation of the analysis device 301, a holding channel 13 to which a part of the solid component separated in the separation chamber 10 is transferred to be stored, a sample overflow chamber 17 for discharging the sample solution remaining in the separation chamber 10, a joint channel 14 for connecting the separation chamber 10 and the sample overflow chamber 17, and a measurement cell 28 for holding the solid component filled in the holding channel 13, and mixing and reacting the solid component with a reagent to measure the absorbance or the turbidity of the mixed solution.

In this fourth embodiment, the reagent to be reacted with the solid component is held in the measurement cell 28. Further, a reagent reaction chamber for making the sample solution react with the reagent and an agitation chamber for performing agitation may be provided between the holding chamber 13 and the measurement cell 28 although they are omitted in this third embodiment.

While in this fourth embodiment the depths of the fluid storage chamber 9, the separation chamber 10, the sample overflow chamber 17, and the measurement cell 28 are 0.3 mm to 2 mm, these depths are adjustable according to the amount of the sample solution or the conditions for absorbance measurement (the optical path length, the measurement wavelength, the reaction concentration of the sample solution, the kind of the reagent, etc.).

The fluid storage chamber 9 is connected to the separation chamber 10, and a previously measured amount of the sample solution is injected from an injection port 8 and stored in the fluid storage chamber 9 as shown in FIG. 13(a), and then the analysis device 301 is rotated to generate a centrifugal force, whereby the sample solution can be transferred to the separation chamber 10 as shown in FIG. 13(b).

In this fourth embodiment, a measurement function for making the separation chamber 10 hold a predetermined amount of the sample solution is not provided. However, in order to reduce the process steps before injection of the sample solution, the separation chamber 10 may be provided with a measurement function for measuring the sample solution, such as a construction for, when the analysis device is rotated, discharging the excess solution into the overflow chamber through the overflow channel from the fluid surface position in the separation chamber at which the required amount of solution can be held, or a construction for providing a capillary channel communicating from the separation chamber to the outside of the analysis device, sucking the sample solution by a capillary force of the capillary channel, measuring the sample solution by the volume of the capillary channel, and transferring the sample solution in the capillary channel to the separation chamber by a centrifugal force.

While in this fourth embodiment the fluid storage chamber 9 and the separation chamber 10 are connected with the same depth, the separation chamber 10 may have an air hole and the fluid storage chamber 9 and the separation chamber 10 may be connected by a capillary channel having a depth of 50 µm to 200 µm to prevent the sample solution from flowing into the separation chamber 10 during injection.

The separation chamber 10 is connected to the holding channel 13 via the joint channel 11 from a position where the separated solution component of the sample solution exists, and further, it is connected to the sample overflow chamber 17 via the joint channel 14 having a siphon shape at a position outer than the radially outermost position of the separation chamber 10.

While the joint channel 11 and the joint channel 14 have the widths of 0.5 mm to 2 mm and the depths of 50 µm to 200 µm, these widths and depths are not especially restricted thereto so long as the joint channel 11 and the joint channel 14 can be filled with the sample solution by a capillary force that is generated when the rotation of the analysis device is stopped.

In the construction of the fourth embodiment, in order to prevent the sample solution from flowing out of the separation chamber 10 beyond the joint position of the joint channel 11 and the holding channel 13 and the curved point of the siphon of the joint channel 14 when the sample solution is transferred from the fluid storage chamber 9 to the separation chamber 10 by rotating the analysis device 401, it is necessary to optimize the size of the separation chamber 10, the joint position of the joint channel 11 and the holding channel 13, the position of the curved point of the siphon of the joint channel 14, and the like on the basis of the amount of the sample solution which has previously been measured. In this fourth embodiment, the joint channel 11 is formed up to a position inner than the fluid surface obtained when the separation chamber 10 holds the predetermined amount of the sample solution, and the joint channel 14 has the curved point of the siphon at a position inner than the fluid surface obtained when the separation chamber 10 holds the predetermined amount of the sample solution, whereby the sample solution transferred from the fluid storage chamber 9 by the centrifugal force is held in the separation chamber 10 and the joint channels 11 and 14 as shown in FIG. 13(b).

The sample solution held in the separation chamber 10 can be separated into a solution component 31 and a solid component 32 as shown in FIG. 13(b) by rotating the analysis device at a high speed for a few minutes. For example, when the sample solution is blood, the blood can be separated into blood plasma and blood cell or high hematocrit blood (blood having a high ratio of blood cell component) by setting the rotation speed at 4000 rpm to 6000 rpm, and performing the rotation for one to five minutes.

The separation chamber 10 is connected to the holding channel 13 via the joint channel 11, and the holding channel 13 is connected to the measurement cell 28 that is positioned outer than the holding channel 13.

The depth of the holding channel 13 is 50 µm to 200 µm, and the separated solution component in the separation chamber 10 is filled in the holding channel 13 by a capillary force when the rotation of the analysis device 301 is stopped.

Since the holding channel 13 can measure the solution by its volume, the allowable volume of the solution component 31 is determined by adjusting the opening area of the holding channel 13 having the predetermined depth, and thereby the holding channel 13 can hold a desired amount of solution.

A gas introduction mechanism (not shown) is connected to the air hole 18 in the state where the rotation of the analysis device 401 is stopped, and a pressure is applied to the boundary between the holding channel 13 and the joint channel 11 by introducing a gas from the air hole 18, and thereby the continuous solution filled in the holding channel 13 is broken at the position of the air hole 18, i.e., at the boundary of the holding channel 13 and the joint channel 11, and then the solution filled in the space between the air hole 18 and the measurement cell 28 flows into the measurement cell 28. The gas introduction mechanism is constituted by a gas generation source such as a compression pump or a high-pressure gas container which can supply a gas such as air or nitrogen, and a piping for connecting the gas generation source and the analysis device 401, and it is detachable from the air hole 18 of the analysis device 401.

Figure 14A:
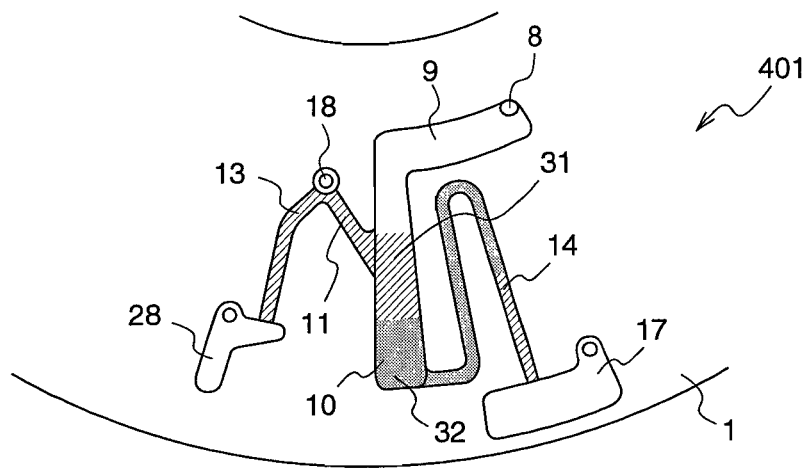
FIG. 14 is a diagram for explaining a measurement process and a measurement cell filling process of the analysis device 401 according to the fourth embodiment.
Figure 14B:
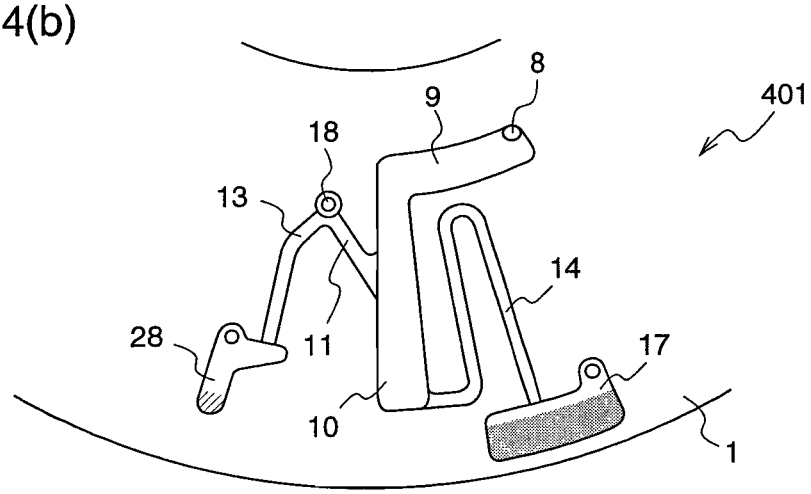

After the holding channel 13 is filled as shown in FIG. 14(a), the solution component held in the holding chamber 13 is transferred to the measurement cell 28 by the pressure of the gas that is introduced into the analysis device 401 as shown in FIG. 14(b).

In this fourth embodiment, the sample solution in the separation chamber 10 is discharged to the sample overflow chamber 17 by the siphon effect of the joint channel 14, in order to prevent the sample solution remaining in the separation chamber 10 from flowing into the holding channel 13 by a capillary force when the rotation of the analysis device 301 is stopped after the solution in the holding channel 13 is transferred to the measurement cell 28, and again flowing into the measurement cell 28 during the next rotation, which causes a change in the mixing ratio of the solution in the measurement cell 28.

Although the solution component that flows in the measurement cell 28 is mixed with the reagent held in the measurement cell 28 due to acceleration/deceleration of rotation or diffusion of the solution while the rotation is stopped, this mixing may be performed using an external force such as vibration.

As for the analysis target component which is included in the solution component mixed with the reagent in the measurement cell 28, its concentration in the sample solution can be calculated by measuring its reaction state with the reagent in absorbance measurement or the like.

According to the analysis device 401 of the fourth embodiment and the analysis apparatus 1000 using the analysis device 401, the analysis device 401 is provided with the fluid storage chamber 9 for holding the sample solution, the holding channel 13 which is connected to the solution storage chamber and holds a part of the sample solution that is transferred from the fluid storage chamber by a capillary force, the fluid holding chamber (measurement cell) 28 for holding the sample solution stored in the holding channel, which is transferred by a pressure difference generated by introduction of a gas from the air hole 18 provided at the solution separation position of the holding channel, and the sample overflow chamber 17 which is connected to the fluid storage chamber via the capillary channel 14 having the siphon structure, and positioned outer than the fluid storage chamber with respect to the axis center of the analysis device when the analysis device is rotated around the axis center. Therefore, the solution component obtained by performing the centrifugal separation can be transferred by a required amount. Further, the sample solution that remains when a part of the sample solution has been transferred can be prevented from flowing in afterward, thereby enhancing the measurement precision of the analysis device.

[Embodiment 5]

Hereinafter, an analysis device 501 according to a fifth embodiment corresponding to claims 4, 11, and 12 and an analysis apparatus 1000 using the analysis device 501 will be described with reference to FIGS. 15 to 18.

The main construction of the analysis device 501 and the construction of the analysis apparatus 1000 on which the analysis device 501 is mounted are identical to those described for the first embodiment, and therefore, repeated description is not necessary.

Figure 15:
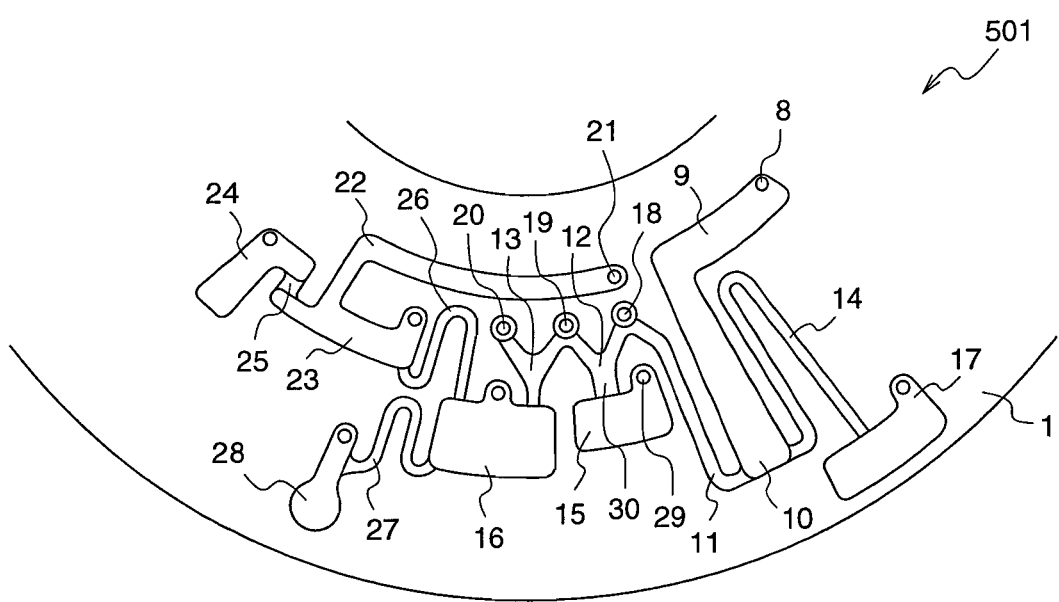
FIG. 15 is a plan view illustrating a microchannel structure of an analysis device 501 according to a fifth embodiment of the present invention.
Figure 16A:
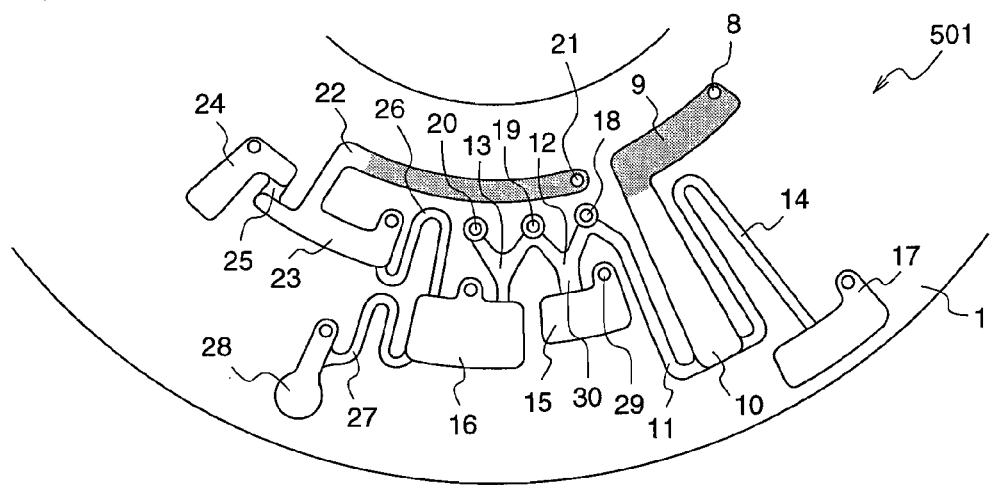
FIG. 16 is a diagram for explaining an injection/separation process of the analysis device 501 according to the fifth embodiment.
Figure 16B:
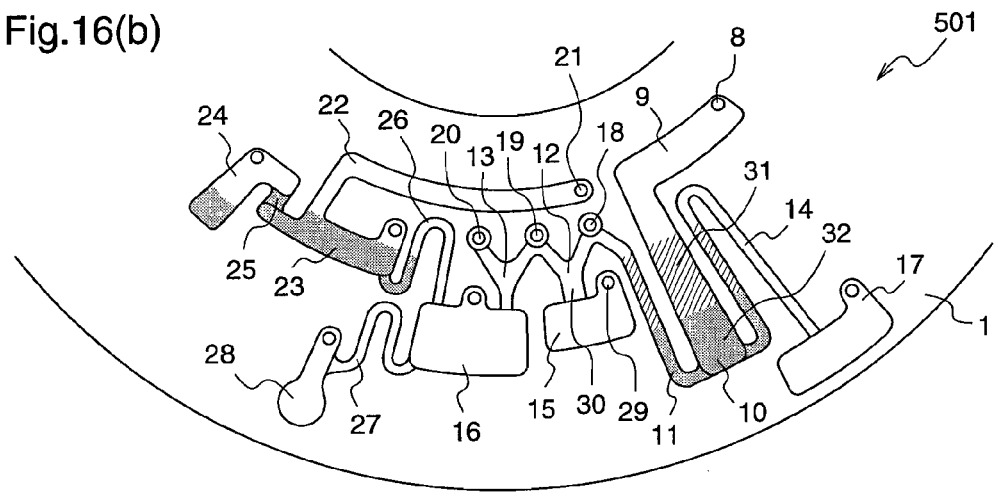
Figure 17A:
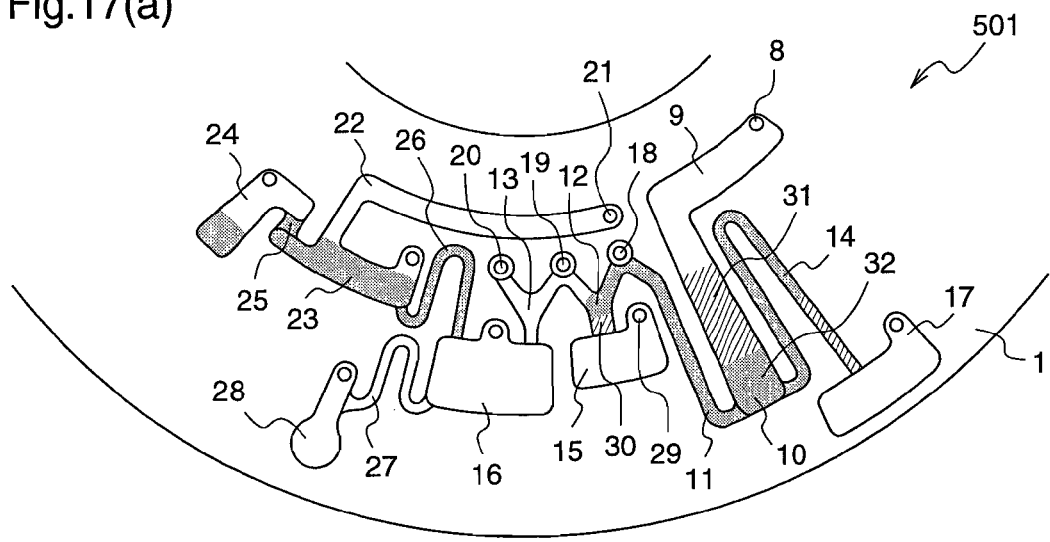
FIG. 17 is a diagram for explaining a measurement process of the analysis device 501 according to the fifth embodiment.

FIG. 15 is a plan view illustrating a microchannel structure in the analysis device 501 of the fifth embodiment. FIGS. 16(a) and 16(b) are diagrams for explaining the injection/separation processes of the analysis device 501, FIGS. 17 (a) and 17 (b) are diagrams for explaining the measurement process of the analysis device 501, and FIGS. 18(a), 18(b), and 18(c) are diagrams for explaining the mixing/measurement cell filling process of the analysis device 501.

With reference to FIG. 15, the microchannel structure of the analysis device 501 according to the fifth embodiment comprises a fluid storage chamber 9 in which a sample solution of an amount required for analysis is injected and stored, a separation chamber 10 for separating the sample solution into a solution component and a solid component by using a centrifugal force that is generated by rotation of the analysis device 501, a holding channel 13 to which a part of the solid component separated in the separation chamber 10 is transferred to be stored, an overflow channel 12 which is connected to the holding channel 13 and the separation chamber 10 via a joint channel 11 for transferring the sample solution stored in the separation chamber 10, an overflow chamber 15 into which the sample solution filled in the overflow channel 12 is discharged, a sample overflow chamber 17 for discharging the sample solution remaining in the separation chamber 10, a joint channel 14 for connecting the separation chamber 10 and the sample overflow chamber 17, a dilute solution storage chamber 22 in which a dilute solution including a denaturant for diluting the solid component or making the solid component react with a specific reagent/antibody is injected and stored, a measurement chamber 23 for holding a predetermined amount of the dilute solution, a mixing chamber 16 for mixing/agitating the solid component from the holding channel 13 with the dilute solution, and a measurement cell 28 for holding the mixed solution, and measuring the absorbance, the turbidity, or the number of cells in the mixed solution.

A reagent reaction chamber for making the sample solution react with the reagent and an agitation chamber for performing agitation may be provided between the mixing chamber 16 and the measurement cell 28 although they are omitted in this fifth embodiment.

While in this fifth embodiment the depths of the fluid storage chamber 9, the separation chamber 10, the sample overflow chamber 17, the overflow chamber 15, the dilute solution storage chamber 22, the measurement chamber 23, the dilute solution overflow chamber 24, the mixing chamber 16, and the measurement cell 28 are 0.3 mm to 2 mm, these depths are adjustable in accordance with the amount of the sample solution or the conditions for absorbance measurement (the optical path length, the measurement wavelength, the reaction concentration of the sample solution, the kind of the reagent, etc.).

The fluid storage chamber 9 is connected to the separation chamber 10, and a previously measured amount of the sample solution is injected from an injection port 8 and stored in the fluid storage chamber 9 as shown in FIG. 16(a), and then the analysis device 501 is rotated to generate a centrifugal force, whereby the sample solution can be transferred to the separation chamber 10 as shown in FIG. 16(b).

In this fifth embodiment, a measurement function for making the separation chamber 10 hold a predetermined amount of the sample solution is not provided. However, in order to reduce the process steps before injection of the sample solution, the separation chamber 10 may be provided with a measurement function for measuring the amount of the sample solution, such as a construction for, when the analysis device is rotated, discharging the excess solution into the overflow chamber through the overflow channel from the fluid surface position in the separation chamber at which the required amount of solution can be held, or a construction for providing a capillary channel communicating from the separation chamber to the outside of the analysis device, sucking the sample solution by a capillary force of the capillary channel, measuring the sample solution by the volume of the capillary channel, and transferring the sample solution in the capillary channel to the separation chamber by a centrifugal force.

While in this fifth embodiment the fluid storage chamber 9 and the separation chamber 10 are connected with the same depth, the separation chamber 10 may be provided with an air hole and the fluid storage chamber 9 and the separation chamber 10 may be connected by a capillary channel having a depth of 50 μm to 200 μm to prevent the sample solution from flowing into the separation chamber 10 during injection.

Further, the separation chamber 10 is connected to the overflow channel 12 via the joint channel 11 from the radially outermost position of the separation chamber 10, and it is connected to the sample overflow chamber 17 via the joint channel 14 having a siphon shape at a position outer than the radially outermost position of the separation chamber 10.

While the joint channel 11 and the joint channel 14 have widths of 0.5 mm to 2 mm and depths of 50 μm to 200 μm, the widths and depths are not especially restricted thereto so long as the joint channel 11 and the joint channel 14 can be filled with the sample solution by a capillary force that is generated when the rotation of the analysis device 501 is stopped.

In the construction of the fifth embodiment, in order to prevent the sample solution from flowing out of the separation chamber 10 beyond the joint position of the joint channel 11 and the overflow channel 12 and the curved point of the siphon of the joint channel 14 when the sample solution is transferred from the fluid storage chamber 9 to the separation chamber 10 by rotating the analysis device 501, it is necessary to optimize the size of the separation chamber 10, the joint position of the joint channel 11 and the overflow channel 12, the position of the curved point of the siphon of the joint channel 14, and the like on the basis of the amount of the sample solution which has previously been measured. For this purpose, in this fifth embodiment, the joint channel 11 is formed up to a position inner than the fluid surface obtained when the separation chamber 10 holds the predetermined amount of the sample solution, and the joint channel 14 has the curved point of the siphon at a position inner than the fluid surface obtained when the separation chamber 10 holds the predetermined amount of the sample solution, whereby the sample solution transferred from the fluid storage chamber 9 by the centrifugal force is held in the separation chamber 10 and the joint channels 11 and 14 as shown in FIG. 16(b).

The sample solution held in the separation chamber 10 can be separated into a solution component 31 and a solid component 32 as shown in FIG. 16(b) by rotating the analysis device at a high speed for a few minutes. For example, when the sample solution is blood, the blood can be separated into blood plasma and blood cell or high hematocrit blood (blood having a high ratio of blood cell component) by setting the rotation speed at 4000 rpm to 6000 rpm, and performing rotation for one to five minutes.

The separation chamber 10 is connected to the holding channel 13 via the joint channel 11 and the overflow channel 12, and the overflow channel 12 is connected to the overflow chamber 15 that is positioned outer than the overflow channel 12, and the holding channel 13 is connected to the mixing chamber 16 that is positioned outer than the holding channel 13.

The depths of the holding channel 13 and the overflow channel 12 are 50 μm to 200 μm, and the separated solid component or high-concentration solid component solution in the separation chamber 10 is filled in the holding channel 13 and the overflow channel 12 by a capillary force when the rotation of the analysis device is stopped.

At this time, although all of the solution component 31 that is separated in the junction channel 11 is transferred to the overflow channel 12 by the capillary force, since the overflow chamber 15 is formed deep, the solution component 31 is not transferred to the overflow chamber 15 but stored in a junction part 30 between the overflow channel 12 and the overflow chamber 15. Thereafter, the solid component 32 that is separated between the joint channel 11 and the separation chamber 10 is transferred to the holding channel 13 via the overflow channel 12.

In this fifth embodiment, since the solution component 31 exists at the inner circumference part of the joint channel 11 connecting the overflow channel 12 and the separation chamber 10 when the sample solution is centrifugally separated in the separation chamber 10 as shown in FIG. 16(b), if the solution component 31 flows into the holding channel 13 as it is, the concentration of the solid component is reduced, thereby causing variations in measurement precision. Therefore, as shown in FIG. 17(a), the opening area of the overflow channel 12 at the junction part 30 between the overflow channel 12 and the overflow chamber 15 is made larger than the opening area of the holding channel 13 at the branching point of the overflow channel 12 and the holding channel 13, thereby to make the solution component 31 flow into the overflow channel 12 with priority. The ratio of the opening area of the overflow channel 12 to that of the holding channel 13 is desired to be 1.5 to 5 times. When the ratio is smaller than 1.5 times, the solution component 31 might flow into the holding channel 13. When it is larger than 5 times, since the area of the overflow channel 12 is too large, the solid component 32 is filled in the overflow channel 12 beyond necessity, leading to a probability that the loss of the solid component 32 might be increased.

While in this fifth embodiment the overflow channel 12 is provided between the joint channel 11 and the holding channel 13, since the solution component 31 can be introduced into the overflow channel 12 with priority by making the opening area of the overflow channel 12 larger than the opening area of the holding channel 13 at the branching point of the holding channel 13 and the overflow channel 12, it is also possible to provide the overflow channel 12 from the junction channel 11 through the holding channel 13.

Since the holding channel 13 and the overflow channel 12 can measure the solution by their volumes, the allowable volume of the solid component 32 is determined by adjusting the opening areas of the holding channel 13 and the overflow channel 12 having the predetermined depth, and thereby each channel can hold a desired amount of the solution. The allowable volume of the overflow channel 12 is designed such that all of the solution component 31 existing in the joint channel 11 can be stored in the overflow channel 12, and the solid component 32 of an amount more than at least 0.5 time of the stored solution component 31 can flow into the channel, thereby preventing the solution component 31 from flowing into the holding channel 13.

By rotating the analysis device 501 to generate a centrifugal force, air is introduced from the air hole 19 and a pressure is applied to the boundary of the holding channel 13 and the overflow channel 12, and thereby the continuous solution filled in the holding channel 13 is broken at the position of the air hole 19, i.e., at the boundary of the holding channel 13 and the overflow channel 12, and then the solution filled in the space between the air hole 19 and the air hole 20 flows into the mixing chamber 16.

Likewise, also the solution filled in the overflow channel 12 is broken at the position between the air hole 18 and the air hole 19, and the solution filled in the space between the position of the air hole 18 and the air hole 19 flows into the overflow chamber 15, while the solution filled in the space between the position of the air hole 18 and the separation chamber 10 is returned into the separation chamber 10 by the centrifugal force.

Figure 17B:
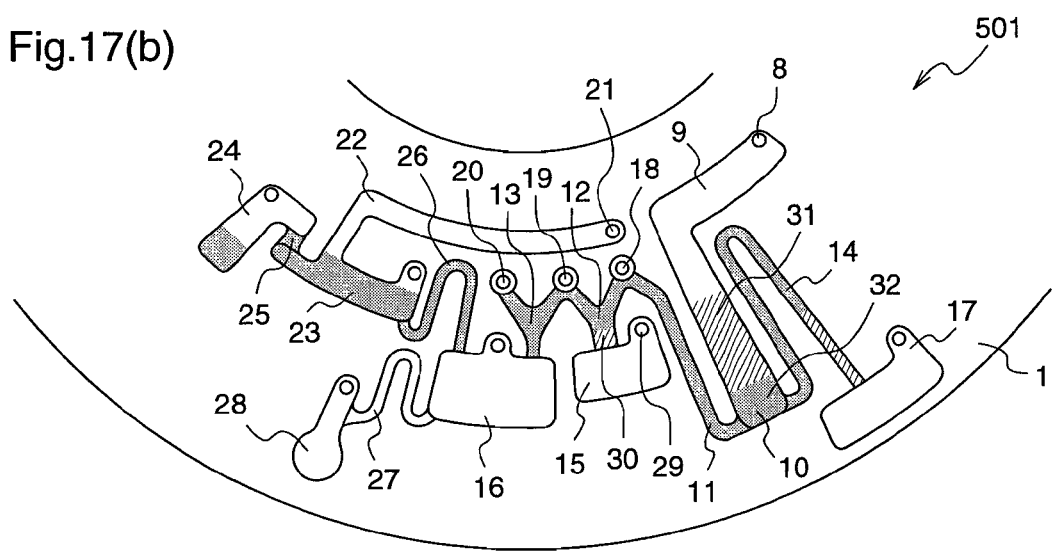
Figure 18A:
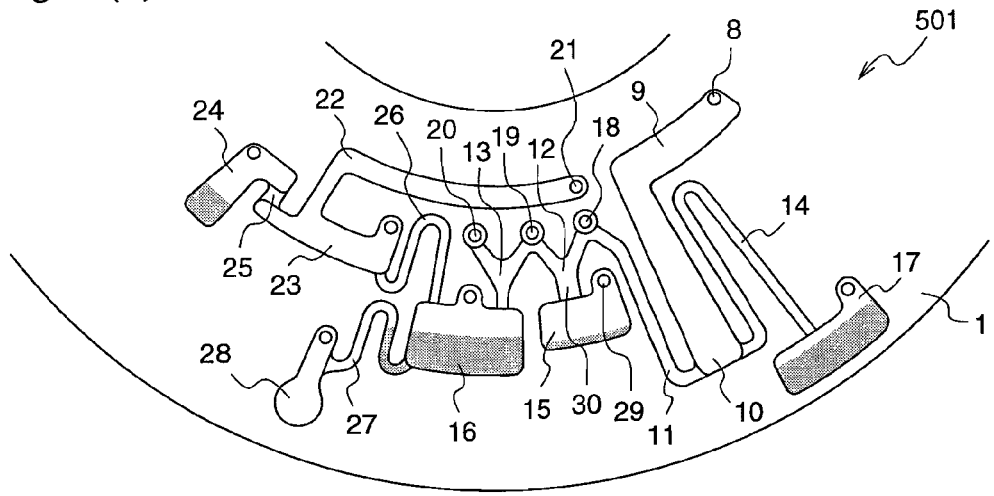
FIG. 18 is a diagram for explaining a mixing/measurement cell filling process of the analysis device 501 according to the fifth embodiment.
Figure 18B:
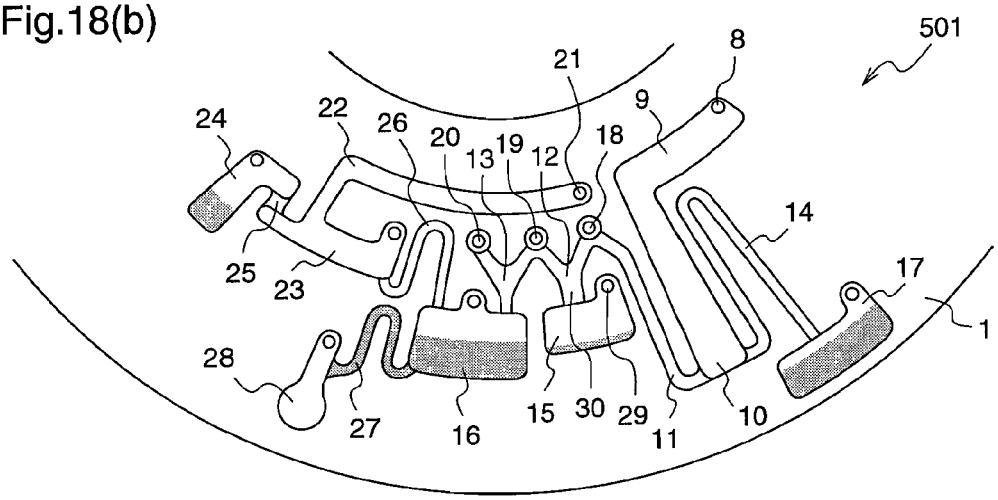
Figure 18C:
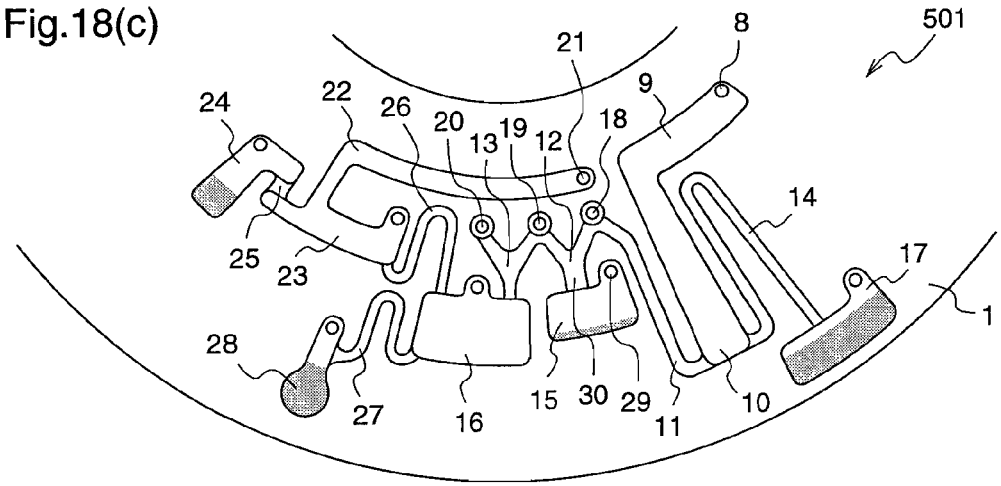

After the holding channel 13 is filled as shown in FIG. 17(b), the analysis device 501 is rotated again, whereby the solid component held in the holding channel 13 is transferred to the mixing chamber 16 by a centrifugal force as shown in FIG. 18(a).

In this fifth embodiment, the sample solution in the separation chamber 10 is discharged to the sample overflow chamber 17 by the siphon effect of the joint channel 14, in order to prevent the sample solution remaining in the separation chamber 10 from flowing into the holding channel 13 by a capillary force when the rotation of the analysis device 301 is stopped after the solution in the holding channel 13 is transferred to the measurement cell 28, and again flowing into the mixing chamber 16 during the next rotation, which causes a change in the mixing ratio of the solution in the mixing chamber 16.

The dilute solution storage chamber 22 is connected to the measurement chamber 23, and the dilute solution can be transferred to the measurement chamber 23 as shown in FIG. 16(b) by injecting the dilute solution from an injection port 21 as shown in FIG. 16(a) and rotating the analysis device.

While in this fifth embodiment the dilute solution storage chamber 22 and the measurement chamber 23 are connected with the same depth, the dilute solution storage chamber 22 and the measurement chamber 23 may be connected by a capillary channel having a depth of 50 μm to 200 μm to prevent the dilute solution from flowing into the measurement chamber 23 when the dilute solution is injected.

The measurement chamber 23 is connected to the flow-in port of the dilute solution overflow chamber 24 which is disposed radially inner than the measurement chamber 23 via the capillary channel 25 from the overflow port that is positioned radially inner than the measurement chamber 23 close to the dilute solution overflow chamber 24, and it is connected to the mixing chamber 16 via the joint channel 26 from a radially outermost position of the measurement chamber 23. The dilute solution overflow chamber 24 is provided with an air hole so as to facilitate flow-in of the dilute solution, and the mixing chamber 16 is also provided with an air hole so as to facilitate flow-in of the dilute solution in the joint channel 26.

The joint channel 26 has a siphon shape having a bent tube that is disposed inner than the distance between the flow-in port of the dilute solution overflow chamber 24 and the surface of the capillary channel 25 from the rotation center of the analysis device. While in this fifth embodiment the capillary channel 25 and the joint channel 26 have the widths of 0.5 mm to 2 mm and the depths of 50 μm to 200 μm, the widths and depths are not particularly restricted thereto so long as the joint channel 26 can be filled with the dilute solution by the capillary force.

Since the measurement chamber 23 and the mixing chamber 16 are thus connected, even when the dilute solution stored in the dilute solution storage chamber 22 is transferred to and filled in the measurement chamber 23 by rotating the analysis device, the dilute solution in the joint channel 26 is filled up to only the position corresponding to the distance from the flow-in port of the dilute solution overflow chamber 24 to the interface of the capillary channel 25 in the radial direction from the rotation center of the analysis device as shown in FIG. 16(b). When the analysis device is stopped after the filling of the measurement chamber 23 is completed, the joint channel 26 is filled with the dilute solution up to the inlet port of the mixing chamber 16 due to the effect of the capillary force as shown in FIG. 17(a). At this time, the dilute solution does not flow into the mixing chamber 16 because the mixing chamber 16 is deep and the capillary force thereof is extremely smaller than that of the joint channel 26.

After the holding channel 13 and the joint channel 26 are filled up as shown in FIG. 17(b), the analysis device is again rotated, whereby the solid component stored in the holding channel 13 and the dilute solution stored in the measurement chamber 23 are transferred to the mixing chamber 16 by the centrifugal force and the siphon effect as shown in FIG. 18(a), and the sample solution filled in the overflow channel 12 is transferred to the overflow chamber 15 while the sample solution stored in the separation chamber 10 is transferred to the sample overflow chamber 17.

Since the mixing chamber 16 and the measurement cell 28 are connected via the joint channel 27 having a siphon shape, the solid component and the dilute solution that flow in the mixing chamber 16 are held in the mixing chamber 16, and the diluted solid component is mixed by acceleration/deceleration of the rotation or diffusion of the solution while the rotation is stopped.

While the joint channel 27 has a width of 0.5 mm to 2 mm and a depth of 50 μm to 200 μm, the width and depth are not especially restricted thereto so long as the joint channel 27 can be filled with the solution by the capillary force.

The joint channel 27 is filled with the mixed solution when the rotation is stopped as shown in FIG. 18(b), and the solution in the mixing chamber 16 can be transferred to the measurement cell 28 by rotating the analysis device again as shown in FIG. 18(c).

When the sample solution is blood, blood cells are destroyed and eluted by mixing the dilute solution and the blood cell component in the mixing chamber 16, and hemoglobin in the blood cells is mixed with the dilute solution. The hemoglobin concentration in the blood can be calculated by measuring the absorbance of the diluted hemoglobin in the measurement cell.

According to the analysis device 501 of the fifth embodiment and the analysis apparatus 1000 using the analysis device 501, the analysis device of the first embodiment is further provided with the mixing chamber 16 which is connected to the holding channel and mixes the solid component with the dilute solution or the reagent solution, and the dilute solution storage chamber 22 which is connected to the mixing chamber and contains the dilute solution or the reagent solution. Therefore, the solid component or the high-concentration solid component solution obtained by performing the centrifugal separation can be transferred by a required amount to the holding channel by performing the same processing as described for the first embodiment, and further, the solid component transferred to the holding channel can be mixed with the dilute solution or the reagent solution and transferred to the measurement cell 28. Further, the sample solution that remains when a part of the sample solution has been transferred can be prevented from flowing in afterward, thereby enhancing the measurement precision of the analysis device.

[Embodiment 6]

Hereinafter, an analysis device 601 according to a sixth embodiment corresponding to claims 4, 11, 12 and 13, and an analysis apparatus 1000 using the analysis device 601 will be described with reference to FIGS. 19 to 22.

The main construction of the analysis device 601 and the construction of the analysis apparatus 1000 on which the analysis device 601 is mounted are identical to those described for the first embodiment, and therefore, repeated description is not necessary.

Figure 19:
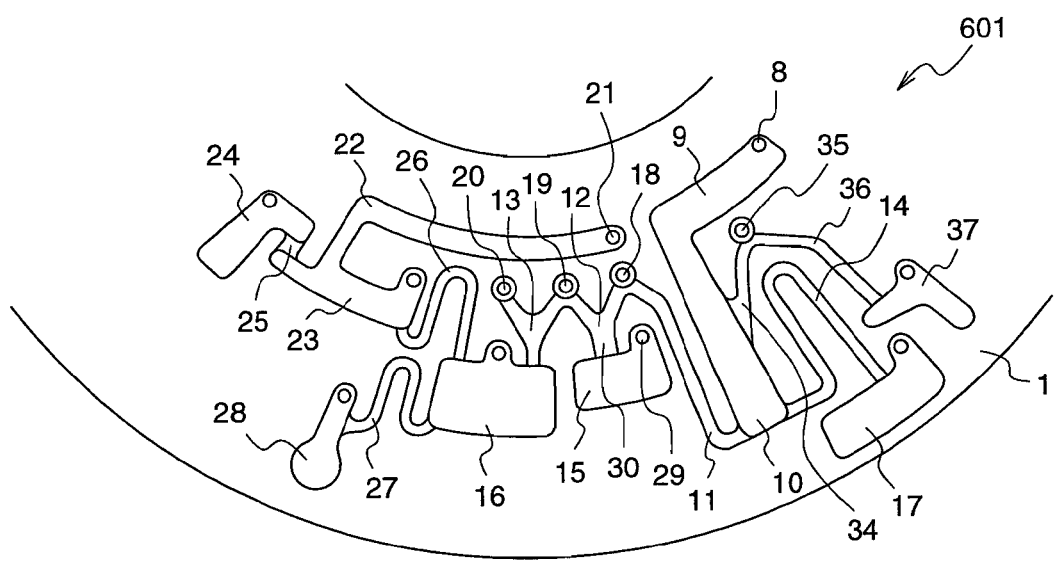
FIG. 19 is a plan view illustrating a microchannel structure of an analysis device 601 according to a sixth embodiment of the present invention.

FIG. 19 is a plan view illustrating a microchannel structure in the analysis device 601 of the sixth embodiment. FIGS. 20(*a*) and 20(*b*) are diagrams for explaining the injection/separation processes of the analysis device 601, FIGS. 21(*a*) and 21(*b*) are diagrams for explaining the measurement process of the analysis device 601, and FIGS. 22(*a*), 22(*b*), and 22(*c*) are diagrams for explaining the mixing/measurement cell filling process of the analysis device 601.

With reference to FIG. 19, the microchannel structure of the analysis device 601 according to the sixth embodiment comprises a fluid storage chamber 9 in which a sample solution of an amount required for analysis is injected and stored, a separation chamber 10 for separating the sample solution into a solution component and a solid component by using a centrifugal force that is generated by rotation of the analysis device 601, a solution component holding channel 36 for holding a part of the solution component that is separated in the separation chamber 10 and transferred via a joint channel 34 connected to the separation chamber 10, a measurement cell 37 for holding the solution component filled in the solution component holding channel 36, and mixing/reacting the solution component with a reagent to measure the absorbance or turbidity of the mixed solution, a holding channel 13 for holding a part of the solid component separated in the separation chamber 10, an overflow channel 12 which is connected to the holding channel 13 and the separation chamber 10 via a joint channel 11 for transferring the sample solution stored in the separation chamber 10, an overflow chamber 15 into which the sample solution filled in the overflow channel 12 is discharged, a sample overflow chamber 17 for discharging the sample solution remaining in the separation chamber 10, a joint channel 14 for connecting the separation chamber 10 and the sample overflow chamber 17, a dilute solution storage chamber 22 in which a dilute solution including a denaturant for diluting the solid component or making the solid component react with a specific reagent/antibody is injected and stored, a measurement chamber 23 for holding a predetermined amount of the dilute solution, a mixing chamber 16 for mixing/agitating the solid component with the dilute solution, and a measurement cell 28 for holding the mixed solution, and measuring the absorbance, the turbidity, or the number of cells in the mixed solution.

In this sixth embodiment, a reagent to be reacted with the solution component is held in the measurement cell 37. Further, a reagent reaction chamber for making the sample solution react with the reagent and an agitation chamber for performing agitation may be provided between the mixing chamber 16 and the measurement cell 28 and between the solution component holding channel 36 and the measurement cell 37, although they are omitted in this sixth embodiment.

While in this sixth embodiment the depths of the fluid storage chamber 9, the separation chamber 10, the sample overflow chamber 17, the overflow chamber 15, the dilute solution storage chamber 22, the measurement chamber 23, the dilute solution overflow chamber 24, the mixing chamber 16, the measurement cell 28, and the measurement cell 37 are 0.3 mm to 2 mm, these depths are adjustable in accordance with the amount of the sample solution or the conditions for absorbance measurement (the optical path length, the measurement wavelength, the reaction concentration of the sample solution, the kind of the reagent, etc.).

The fluid storage chamber 9 is connected to the separation chamber 10, and a previously measured amount of the sample solution is injected from an injection port 8 and stored in the fluid storage chamber 9 as shown in FIG. 20(*a*), and then the analysis device 601 is rotated to generate a centrifugal force, whereby the sample solution can be transferred to the separation chamber 10 as shown in FIG. 20(*b*).

In this sixth embodiment, a measurement function for making the separation chamber 10 hold a predetermined amount of the sample solution is not particularly provided. However, in order to reduce the process steps before injection of the sample solution, the separation chamber 10 may be provided with a measurement function for measuring the amount of the sample solution, such as a construction for, when the analysis device is rotated, discharging the excess solution into the overflow chamber through the overflow channel from the fluid surface position in the separation chamber at which the required amount of solution can be held, or a construction for providing a capillary channel communicating from the separation chamber to the outside of the analysis device, sucking the sample solution by a capillary force of the capillary channel, measuring the sample solution by the volume of the capillary channel, and transferring the sample solution in the capillary channel to the separation chamber by a centrifugal force.

While in this sixth embodiment the fluid storage chamber 9 and the separation chamber 10 are connected with the same depth, the separation chamber 10 may be provided with an air hole and the fluid storage chamber 9 and the separation chamber 10 may be connected by a capillary channel having a depth of 50 μm to 200 μm to prevent the sample solution from flowing into the separation chamber 10 during injection.

The separation chamber 10 is connected to the solution component holding channel 36 via the joint channel 34 from the position where the separated solution component of the sample solution exists, and it is connected to the overflow channel 12 via the joint channel 11 from the radially outermost position of the separation chamber 10, and further, it is connected to the sample overflow chamber 17 via the joint channel 14 having a siphon shape at the position outer than the radially outermost position of the separation chamber 10.

While the joint channel 11, the joint channel 34, and the joint channel 14 have widths of 0.5 mm to 2 mm and depths of 50 μm to 200 μm, the widths and depths are not especially restricted thereto so long as the joint channels 11, 34, and 14 can be filled with the sample solution by a capillary force that is generated when the rotation of the analysis device 601 is stopped.

In the construction of the sixth embodiment, in order to prevent the sample solution from flowing out of the separation chamber 10 beyond the joint position of the joint channel 11 and the overflow channel 12, the joint position of the joint channel 34 and the solution component holding channel 36, and the curved point of the siphon of the joint channel 14 when the sample solution is transferred from the fluid storage chamber 9 to the separation chamber 10 by rotating the analysis device 601, it is necessary to optimize the size of the separation chamber 10, the joint position of the joint channel 11 and the overflow channel 12, the joint position of the joint channel 34 and the solution component holding channel 36, and the position of the curved point of the siphon of the joint channel 14, on the basis of the amount of the sample solution which has previously been measured. For this purpose, in this sixth embodiment, the joint channel 11 and the joint channel 34 are formed up to a position inner than the fluid surface obtained when the separation chamber 10 holds the predetermined amount of the sample solution, and further, also the joint channel 14 has the curved point of the siphon at a position inner than the fluid surface that is obtained when the separation chamber 10 holds the predetermined amount of the sample solution, whereby the sample solution transferred from the fluid storage chamber 9 by the centrifugal force is held in the separation chamber 10 and the joint channels 11, 34, and 14 as shown in FIG. 20(b).

Figure 20A:
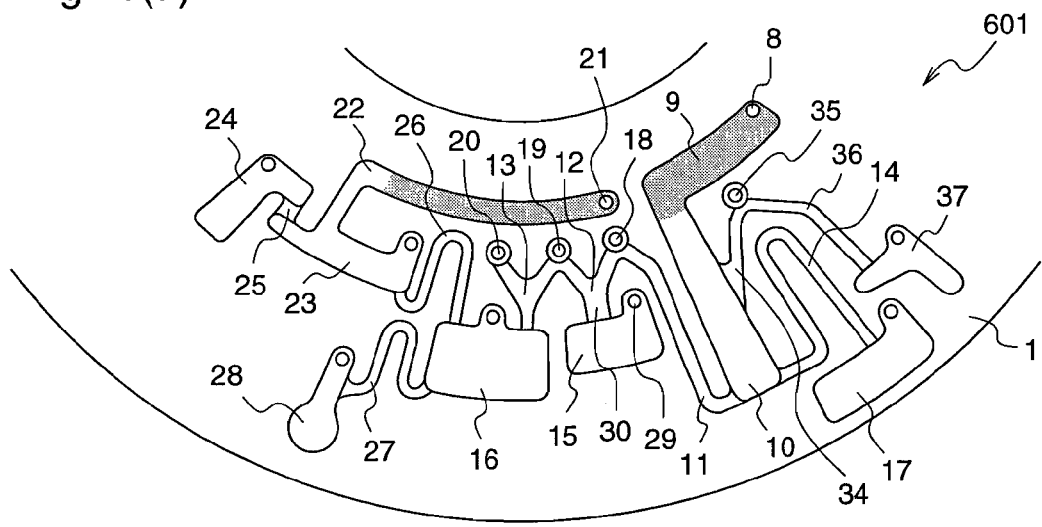
FIG. 20 is a diagram for explaining an injection/separation process of the analysis device 601 according to the sixth embodiment.
Figure 20B:
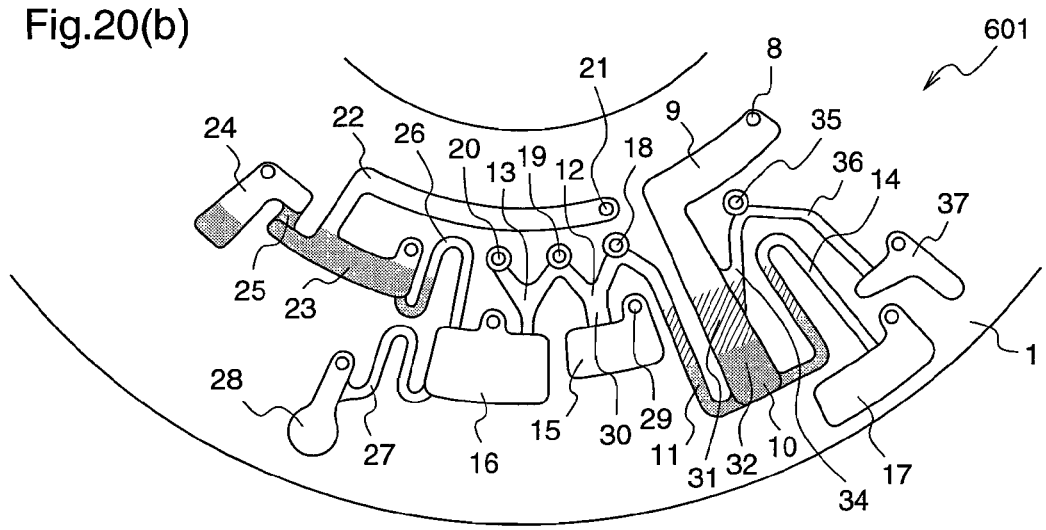

The sample solution held in the separation chamber 10 can be separated into a solution component 31 and a solid component 32 as shown in FIG. 20(b) by rotating the analysis device at a high speed for a few minutes. For example, when the sample solution is blood, the blood can be separated into blood plasma and blood cells or high hematocrit blood (blood having a high ratio of blood cell component) by setting the rotation speed at 4000 rpm to 6000 rpm, and performing the rotation for one to five minutes.

The separation chamber 10 is connected to the holding channel 13 via the joint channel 11 and the overflow channel 12 and connected to the solution component holding channel 36 via the joint channel 34, the overflow channel 12 is connected to the overflow chamber 15 that is positioned outer than the overflow channel 12, the holding channel 13 is connected to the mixing chamber 16 that is positioned outer than the holding channel 13, and the solution component holding channel 36 is connected to the measurement cell 37 that is positioned outer than the solution component holding channel 36.

The depths of the holding channel 13 and the overflow channel 12 are 50 μm to 200 μm, and the separated solid component or high-concentration solid component solution in the separation chamber 10 is filled in the holding channel 13 and the overflow channel 12 by a capillary force when the rotation of the analysis device is stopped.

At this time, while all of the solution component 31 that is separated in the junction channel 11 is initially transferred to the overflow channel 12 by the capillary force, since the overflow chamber 15 is formed deep, the solution component 31 is not transferred to the overflow chamber 15 but stored in a junction part 30 between the overflow channel 12 and the overflow chamber 15. Thereafter, the solid component 32 that is separated between the joint channel 11 and the separation chamber 10 is transferred to the holding channel 13 via the overflow channel 12.

Figure 21A:
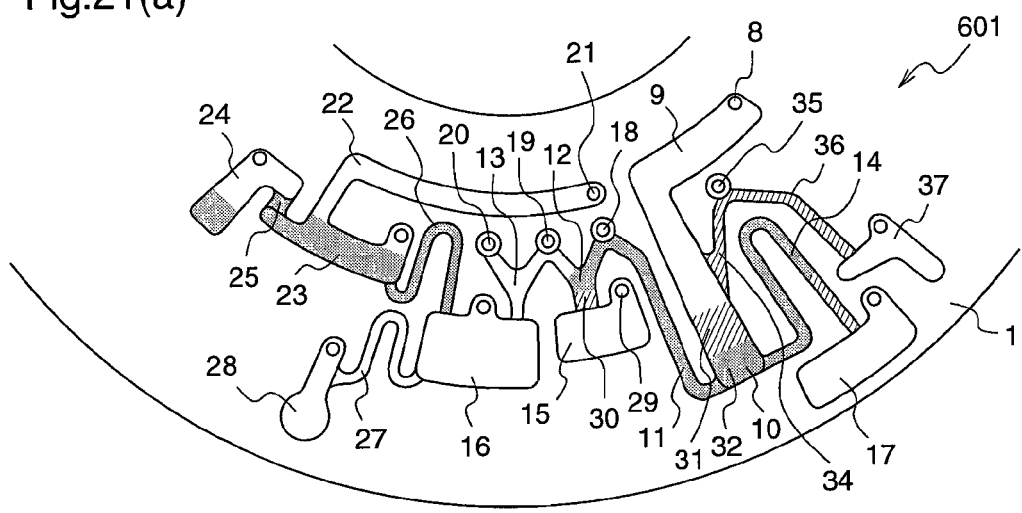
FIG. 21 is a diagram for explaining a measurement process of the analysis device 601 according to the sixth embodiment.

In this sixth embodiment, since the solution component 31 exists at the inner circumference part of the joint channel 11 connecting the overflow channel 12 and the separation chamber 10 when the sample solution is centrifugally separated in the separation chamber 10 as shown in FIG. 20(b), if the solution component 31 flows into the holding channel 13 as it is, the concentration of the solid component is reduced, which causes variations in the measurement precision. Therefore, as shown in FIG. 21(a), at the branching point of the overflow channel 12 and the holding channel 13, the opening area of the overflow channel 12 at the junction part 30 between the overflow channel 12 and the overflow chamber 15 is made larger than the opening area of the holding channel 13, whereby the solution component 31 flow into the overflow channel 12 with priority. The opening area of the overflow channel 12 is desired to be 1.5 to 5 times larger than that of the holding channel 13. When the ratio is smaller than 1.5, the solution component 31 might flow into the holding channel 13. When it is larger than 5, since the area of the overflow channel 12 becomes too large, the solid component 32 is filled in the channel beyond necessity, resulting in an increase in the loss of the solid component 32.

While in this sixth embodiment the overflow channel 12 is provided between the joint channel 11 and the holding channel 13, since the solution component 31 can be introduced into the overflow channel 12 with priority by making the opening area of the overflow channel 12 larger than the opening area of the holding channel 13 at the branching point of the holding channel 13 and the overflow channel 12 as in this sixth embodiment, it is also possible to provide the overflow channel 12 from the junction channel 11 through the holding channel 13.

Since the holding channel 13 and the overflow channel 12 can measure the solution by their volumes, the allowable volume of the solid component 32 is determined by adjusting the opening areas of the holding channel 13 and the overflow channel 12 having the predetermined depth, and thereby each channel can hold a desired amount of the solution. The allowable volume of the overflow channel 12 is designed such that the overflow channel 12 can hold all of the solution component 31 existing in the joint channel 11, and the solid component 32 of an amount larger than at least 0.5 time of the stored solution component 31 can flow into the chamber, thereby preventing the solution component 31 from flowing into the holding channel 13.

The depth of the solution component holding channel 36 is 50 μm to 200 μm, and the separated solution component in the separation chamber 19 is filled in the solution component holding channel 36 by the capillary force when the rotation of the analysis device is stopped.

Since the solution component holding channel 36 can measure the solution by its volume, the allowable volume of the solution component 31 is determined by adjusting the opening area of the solution component holding channel 36 having the predetermined depth, and thereby the channel 36 can hold a required amount of the solution.

By rotating the analysis device 601 to generate a centrifugal force, air is introduced from the air hole 19 and a pressure is applied to the boundary between the holding channel 13 and the overflow channel 12, and thereby the continuous solution filled in the holding channel 13 is broken at the position of the air hole 19, i.e., at the boundary of the holding channel 13 and the overflow channel 12, and then the solution filled in the space between the air hole 19 and the air hole 20 flows into the mixing chamber 16.

Likewise, the solution filled in the overflow channel 12 is also broken at the position between the air hole 18 and the air hole 19, and the solution filled in the space between the position of the air hole 18 and the air hole 20 flows into the overflow chamber 15, while the solution filled in the space between the position of the air hole 18 and the separation chamber 10 is returned into the separation chamber 10 by the centrifugal force.

Further, the solution filled in the solution component holding channel 36 is also broken at the position of the air hole 35, and the solution filled in the space between the position of the air hole 35 and the measurement cell 37 flows into the measurement cell 37, while the solution filled in the space between the position of the air hole 35 and the separation chamber 10 is returned into the separation chamber 10 by the centrifugal force.

Figure 21B:
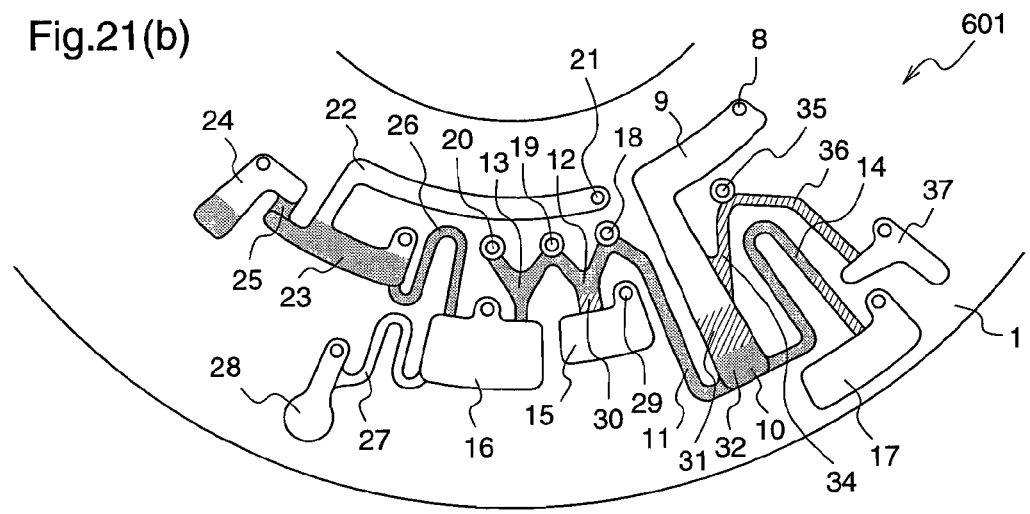

After the holding channel 13 and the solution component holding channel 36 are filled as shown in FIG. 21(b), the analysis device 601 is rotated again, whereby the solid component held in the holding channel 13 and the solution component held in the solution component holding channel 36 are transferred to the mixing chamber 16 and the measurement cell 37, respectively, by a centrifugal force as shown in FIG. 21(a).

In this fifth embodiment, the sample solution in the separation chamber 10 is discharged to the sample overflow chamber 17 by the siphon effect of the joint channel 14, in order to prevent the sample solution remaining in the separation chamber 10 from flowing into the holding channel 13 by a capillary force when the rotation of the analysis device 301 is stopped after the solution in the holding channel 13 is transferred to the measurement cell 28, and again flowing into the mixing chamber 16 during the next rotation, which causes a change in the mixing ratio of the solution in the mixing chamber 16.

The dilute solution storage chamber 22 is connected to the measurement chamber 23, and the dilute solution can be transferred to the measurement chamber 23 as shown in FIG. 20(b) by injecting/storing the dilute solution from an injection port 21 and rotating the analysis device 601 as shown in FIG. 20(a).

While in this sixth embodiment the dilute solution storage chamber 22 and the measurement chamber 23 are connected with the same depth, the dilute solution storage chamber 22 and the measurement chamber 23 may be connected by a capillary channel having a depth of 50 µm to 200 µm to prevent the dilute solution from flowing into the measurement chamber 23 when the dilute solution is injected.

The measurement chamber 23 is connected to the flow-in port of the dilute solution overflow chamber 24 which is disposed radially inner than the measurement chamber 23 via the capillary channel 25 from the overflow port that is positioned radially inner than the measurement chamber 23 close to the dilute solution overflow chamber 24, and it is connected to the mixing chamber 16 via the joint channel 26 from a radially outermost position of the measurement chamber 23. The dilute solution overflow chamber 24 is provided with an air hole so as to facilitate flow-in of the dilute solution, and the mixing chamber 16 is also provided with an air hole so as to facilitate flow-in of the dilute solution in the joint channel 26.

The joint channel 26 has a siphon shape having a bent tube that is disposed inner than the distance between the flow-in port of the dilute solution overflow chamber 24 and the surface of the capillary channel 25 from the rotation center of the analysis device. While in this sixth embodiment the capillary channel 25 and the joint channel 26 have the widths of 0.5 mm to 2 mm and the depths of 50 µm to 200 µm, the widths and depths are not particularly restricted thereto so long as the joint channel 26 can be filled with the dilute solution by the capillary force.

Since the measurement chamber 23 and the mixing chamber 16 are thus connected, even when the dilute solution stored in the dilute solution storage chamber 22 is transferred to and filled in the measurement chamber 23 by rotating the analysis device, the dilute solution in the joint channel 26 is filled up to only the position corresponding to the distance from the flow-in port of the dilute solution overflow chamber 24 to the interface of the capillary channel 25 in the radial direction from the rotation center of the analysis device as shown in FIG. 21(b). When the analysis device 601 is stopped after the filling of the measurement chamber 23 is completed, the joint channel 26 is filled with the dilute solution up to the inlet port of the mixing chamber 16 due to the effect of the capillary force as shown in FIG. 21(a). At this time, the dilute solution does not flow into the mixing chamber 16 because the mixing chamber 16 is deep and the capillary force thereof is extremely smaller than that of the joint channel 26.

Figure 22A:
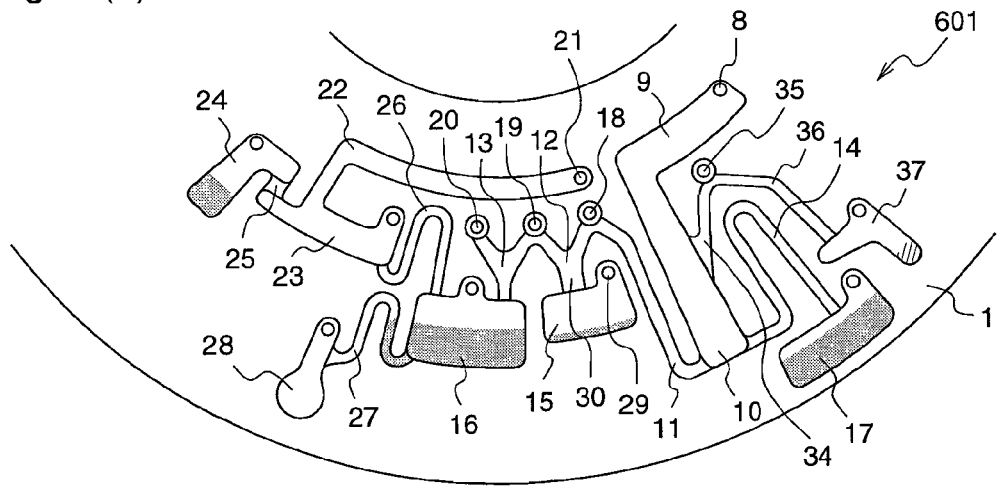
FIG. 22 is a diagram for explaining a mixing/measurement cell filling process of the analysis device 601 according to the sixth embodiment.

After the holding channel 13, the solution component holding channel 36, and the joint channel 26 are filled up as shown in FIG. 21(b), the analysis device 601 is again rotated, whereby the solid component stored in the holding channel 13, the solution component stored in the solution component holding channel 36, and the dilute solution stored in the measurement chamber 23 are transferred to the mixing chamber 16 and the measurement cell 37 by the centrifugal force and the siphon effect as shown in FIG. 22(a), and the sample solution filled in the overflow channel 12 is transferred to the overflow chamber 15 while the sample solution stored in the separation chamber 10 is transferred to the sample overflow chamber 17.

While the solution component that flows into the measurement cell 37 is mixed with the reagent that is held in the measurement cell 37 by acceleration/deceleration of the rotation or diffusion of the solution while the rotation is stopped, this mixing may be performed by using an external force such as vibration.

As for the analysis target component included in the solution component mixed with the reagent in the measurement cell 37, its concentration in the sample solution can be calculated by measuring its reaction state with the reagent in absorbance measurement or the like.

Since the mixing chamber 16 and the measurement cell 28 are connected via the joint channel 27 having the siphon shape, the solid component and the dilute solution that flow into the mixing chamber 16 are held in the mixing chamber 16, and the diluted solid component is mixed by acceleration/deceleration of the rotation or diffusion of the solution while the rotation is stopped.

While the joint channel 27 has a width of 0.5 mm to 2 mm and a depth of 50 µm to 200 µm, the width and depth are not especially restricted thereto so long as the joint channel 27 can be filled with the solution by the capillary force.

Figure 22B:
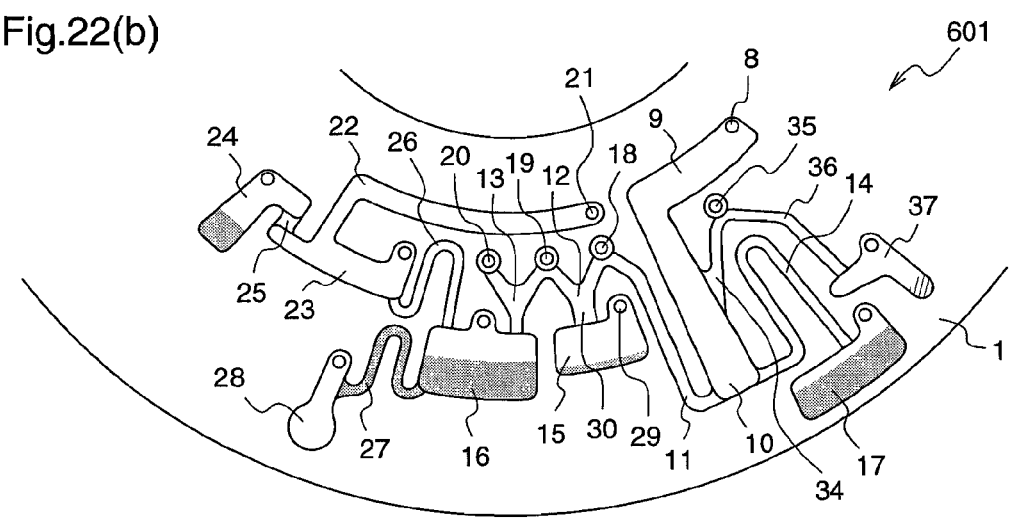
Figure 22C:
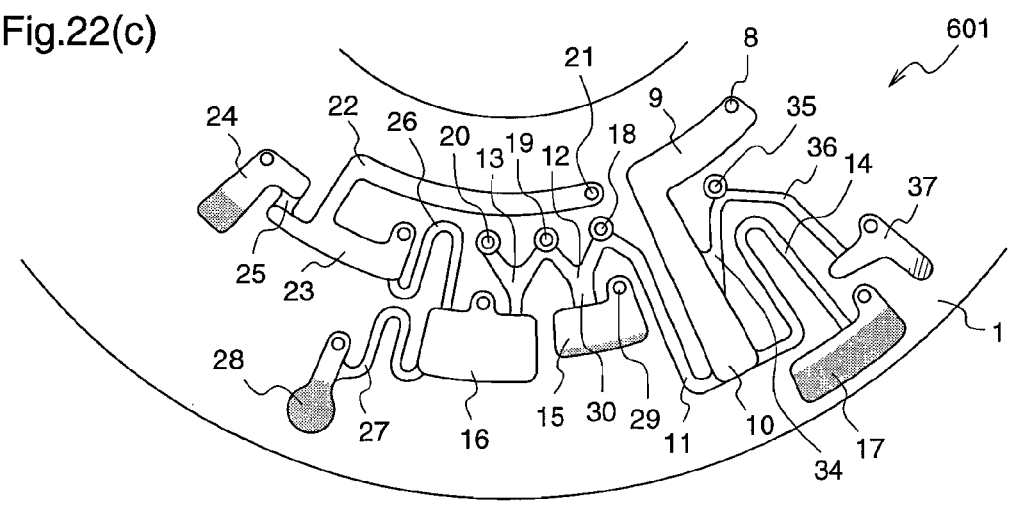
Figure 23:
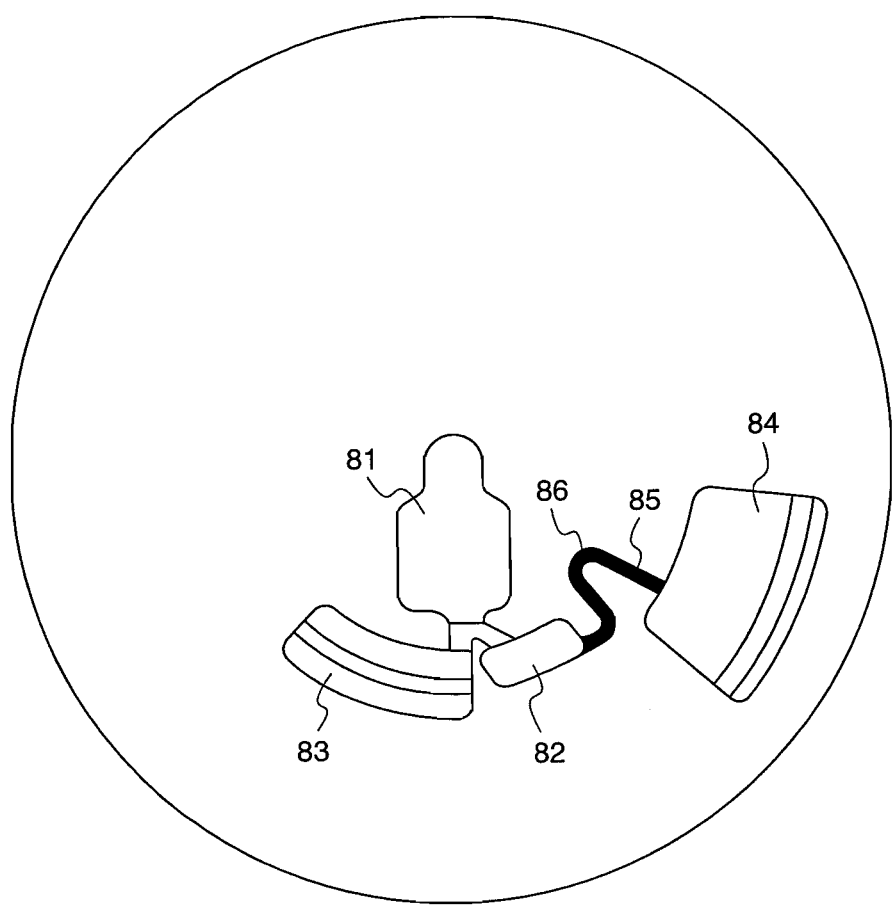
FIG. 23 is a diagram for explaining a sample solution separation/transfer method utilizing a centrifugal force according to the prior art.

The joint channel 27 is filled with the mixed solution when the rotation is stopped as shown in FIG. 22(b), and the solution in the mixing chamber 16 can be transferred to the measurement cell 28 by rotating the analysis device again as shown in FIG. 18(c).

When the sample solution is blood, blood cells are destroyed and eluted by mixing the dilute solution and the blood cell component in the mixing chamber 16, and hemoglobin in the blood cells is mixed with the dilute solution. The hemoglobin concentration in the blood can be calculated by measuring the absorbance of the diluted hemoglobin in the measurement cell 28. According to the analysis device 601 of the sixth embodiment and the analysis apparatus 1000 using the analysis device 601, the analysis device of the first embodiment is further provided with the mixing chamber 16 which is connected to the holding channel and mixes the solid component with the dilute solution or the reagent solution, and the dilute solution storage chamber 22 which is connected to the mixing chamber and contains the dilute solution or the reagent solution, and furthermore, the analysis device is provided with the solution component holding channel 36 which is connected to the separation chamber and holds a part of the solution component separated from the sample solution in the separation chamber, and the measurement cell 37 which holds the solution component filled in the solution component holding channel and mixes/reacts the solution component with the reagent to measure the absorbance or the turbidity of the mixed solution. Therefore, the solid component or the high-concentration solid component solution obtained by performing the centrifugal separation can be transferred by a required amount to the holding channel while the solution component can be transferred to the measurement cell 37 by performing the same processings as described for the first and fifth embodiments, and further, the solid component transferred to the holding channel can be mixed with the dilute solution or the reagent solution and transferred to the measurement cell 28. Further, the sample solution that remains when a part of the sample solution has been transferred can be prevented from flowing in afterward, thereby enhancing the measurement precision of the analysis device.

The analysis device according to the present invention and the analysis apparatus using the analysis device have an effect of transferring only a desired amount of the solution component, solid component, or high-concentration solid component solution which are obtained by performing centrifugal separation, and an effect of preventing a sample solution that remains after a part of the sample solution has been transferred from flowing in afterward, and therefore, they are applicable to a method of collecting a solution component or a solid component in an analysis device used for component measurement of a biological fluid in an optical analysis apparatus.

What is claimed is:

1. An analysis device for storing and transferring a sample solution to be analyzed, said device comprising:
    a fluid storage chamber configured to have the sample solution injected and stored therein;
    a separation chamber configured to separate the sample solution into a solution component and a solid component by applying a centrifugal force generated by rotation of the analysis device;
    a holding channel configured to have a capillary force for holding a part of the solution component separated by the separation chamber;
    a first joint channel that joins the separation chamber and the holding channel, the first joint channel configured to have a capillary force;
    an air hole disposed on a boundary region between the first joint channel and the holding channel;
    a measurement cell configured to hold the part of the solution component separated by the separation chamber and transferred from the holding channel, the solution component being transferred by an external force;
    a sample overflow chamber positioned outwardly of the separation chamber with respect to an axial center of the analysis device when the analysis device is rotated around the axial center; and
    a second joint channel configured and arranged to collect the sample solution other than the part of the solution component into the sample overflow chamber, the second joint channel configured to have a capillary force, and the second joint channel having a siphon structure with a bend portion which is arranged so as to be positioned inwardly of a solution level of the sample solution stored in the separation chamber with respect to the axial center of the analysis device,
    wherein the solution level corresponds to a predetermined solution level of the sample solution when held in the separation chamber.

2. An analysis device as defined in claim 1 wherein the external force is the centrifugal force that is generated by rotation of the analysis device.

3. An analysis device as defined in claim 2 wherein the external force is a pressure that is generated by introduction of a gas from an air hole provided at a fluid separation position of the holding channel.

4. An analysis device as defined in claim 1 wherein the holding channel is configured to measure the solution to be held by a volume thereof.

5. An analysis device for storing and transferring a sample solution to be analyzed, said device comprising:
    a fluid storage chamber configured to have the sample solution injected and stored therein;
    a separation chamber configured to separate the sample solution into a solution component and a solid component by applying a centrifugal force generated by rotation of the analysis device;
    a holding channel configured to have a capillary force for holding a part of the solid component separated by the separation chamber;
    a first joint channel that joins the separation chamber and the holding channel, the first joint channel configured to have a capillary force;
    an air hole disposed on a boundary region between the first joint channel and the holding channel;
    a measurement cell configured to hold the part of the solid component separated by the separation chamber and transferred from the holding channel, the solid component being transferred by an external force;
    a sample overflow chamber positioned outwardly of the separation chamber with respect to an axial center of the analysis device when the analysis device is rotated around the axial center; and
    a second joint channel configured and arranged to collect the sample solution other than the part of the solid component into the sample overflow chamber, the second joint channel configured to have a capillary force, and the second joint channel having a siphon structure with a bend portion which is arranged so as to be positioned inwardly of a solution level of the sample solution stored in the separation chamber with respect to the axial center of analysis device,
    wherein the solution level corresponds to a predetermined solution level of the sample solution when held in the separation chamber.

6. An analysis device as defined in claim 5 further including
    a solution component holding channel connected to the separation chamber, for holding a part of the solution component separated from the sample solution in the separation chamber, and
    a measurement cell configured to hold the solution component filled in the solution component holding channel, mix/react the solution component with a reagent, and measure an absorbance or a turbidity of the mixed solution.

7. An analysis apparatus comprising:
    the analysis device defined in claim 2; and:
    a rotation drive device configured to rotate the analysis device around an axial center thereof.

8. An analysis apparatus on which the analysis device defined in claim 3 is mounted, including
    a rotation drive device configured to rotate the analysis device around an axial center thereof, and
    a gas introduction mechanism configured to transfer the solution in the analysis device,
    the rotation drive operable to
    transfer a sample solution to an outer circumference part of the fluid storage chamber by rotating the analysis device in which the sample solution is stored in the fluid storage chamber,
    suck the sample solution out of the separation chamber by a capillary force and store the sample solution in the holding channel by stopping the rotation of the analysis device,
    suck the sample solution out of the separation chamber by a capillary force and store the sample solution in the first joint channel having the siphon structure connected to the sample overflow chamber, and
    the gas introduction mechanism configured to connect to the air hole disposed at the fluid separation position of the holding channel, and to the air hole disposed at the boundary region separation chamber, and supply a gas via the air hole disposed at the boundary region so that the sample solution filled in the holding channel is separated at the fluid separation position and transferred to the measurement cell, and discharge the sample solution in the fluid storage chamber into the sample overflow chamber by the siphon structure of the first joint channel.

9. An analysis device as defined in claim 5 further including:

an overflow channel disposed between the holding channel and the first joint channel; and another overflow chamber connected to the overflow channel.

10. An analysis device as defined in claim 5 wherein another overflow chamber is connected to an overflow channel via a junction part, the holding channel and the overflow channel have a capillary tube size which is capable of generating a capillary flow of fluid, and an opening area of the overflow channel at the junction part between the overflow channel and the another overflow chamber is larger than that of the holding channel.

11. An analysis device as defined in claim 1 wherein the air hole is configured and arranged so as to enable air to enter the air hole and such that the external force is capable of applying pressure at the boundary of the holding channel and the first joint channel thereby transferring a predetermined amount of solution from the holding channel to the measurement cell.

12. An analysis device as defined in claim 1 wherein the second joint channel is configured and arranged to collect the sample solution other than the part of the solution component into the sample overflow chamber so as to prevent the sample solution other than the part of the solution component from entering the first joint channel.

* * * * *